United States Patent
Gormley et al.

(10) Patent No.: US 11,453,875 B2
(45) Date of Patent: Sep. 27, 2022

(54) SURFACE-BASED TAGMENTATION

(71) Applicant: ILLUMINA CAMBRIDGE LIMITED, Saffron Walden (GB)

(72) Inventors: Niall Anthony Gormley, Saffron Walden (GB); Avgousta Ioannou, Saffron Walden (GB); Rosamond Jackson, Saffron Walden (GB); Natalie Morrell, Saffron Walden (GB)

(73) Assignee: ILLUMINA CAMBRIDGE LIMITED, Essex (GB)

( * ) Notice: Subject to any disclaimer, the term of this patent is extended or adjusted under 35 U.S.C. 154(b) by 478 days.

(21) Appl. No.: 15/575,803

(22) PCT Filed: May 27, 2016

(86) PCT No.: PCT/GB2016/051563
§ 371 (c)(1),
(2) Date: Nov. 20, 2017

(87) PCT Pub. No.: WO2016/189331
PCT Pub. Date: Dec. 1, 2016

(65) Prior Publication Data
US 2018/0155709 A1 Jun. 7, 2018

Related U.S. Application Data

(60) Provisional application No. 62/167,463, filed on May 28, 2015.

(51) Int. Cl.
| C12N 15/10 | (2006.01) |
| C12Q 1/6806 | (2018.01) |
| C12N 9/22 | (2006.01) |
| C40B 50/14 | (2006.01) |

(52) U.S. Cl.
CPC .......... *C12N 15/1065* (2013.01); *C12N 9/22* (2013.01); *C12N 15/1017* (2013.01); *C12Q 1/6806* (2013.01); *C40B 50/14* (2013.01)

(58) Field of Classification Search
CPC ...... C12N 9/1241; C12N 11/02; C12N 11/06; C12N 11/14; C12N 15/1065; C12Q 1/6806; C12Q 1/6869–1/6874; B01J 37/32; B01J 37/0236; B01J 37/0045; B01J 37/0054
See application file for complete search history.

(56) References Cited

U.S. PATENT DOCUMENTS

| 5,925,545 | A | 7/1999 | Reznikoff et al. | |
| 7,919,294 | B2* | 4/2011 | Franco De Sarabia Rosado | C12N 9/96 |
| | | | | 435/188 |
| 9,738,923 | B2* | 8/2017 | Johnson | C12Q 1/6806 |
| 2014/0093916 | A1* | 4/2014 | Belyaev | C12N 9/22 |
| | | | | 435/91.2 |
| 2014/0194324 | A1* | 7/2014 | Gormley | B01J 19/0046 |
| | | | | 506/17 |

FOREIGN PATENT DOCUMENTS

| EP | 2712931 | 4/2014 |
| WO | 2010001162 A1 | 1/2010 |
| WO | 2013/131962 | 9/2013 |
| WO | 2014/108810 | 7/2014 |
| WO | 2015/189636 | 12/2015 |
| WO | 2016/061517 | 4/2016 |

OTHER PUBLICATIONS

Ahlford et al. Dried reagents for multiplex genotyping by tag-array minisequencing to be used in microfluidic devices. Analyst, vol. 135, pp. 2377-2385, 2010, including pp. 1-8 of Electronic Supplementary Information for Analyst. (Year: 2010).*
International Search Report and Written Opinion for Application No. PCT/GB2016/051563, dated Nov. 11, 2016.
Kim et al., "A Microfluidic DNA Library Preparation Platform for Next-Generation Sequencing," PLOS One, 8(2), 2013, e68988.
Tatsumi et al., "Optimization and cost-saving in tagmentation-based mate-pair library preparation and sequencing—Supplementary Material," BioTechniques 2015, 58(5), 1-2.
Cao et al., Effect of Freezing and Thawing Rates on Denaturation of Proteins in Aqueous Solutions, Biotechnology and Bioengineering, 82(6), pp. 684-690, Jun. 20, 2003.
Garibyan et al., Research Techniques Made Simple: Polymerase Chain Reaction (PCR), Journal of Investigative Dermatology, 133(3), pp. 1-8, Mar. 2013.
Wu et al., Advance Understanding of Buffer Behavior during Lyophilization, Lyophilized Biologies and Vaccines, pp. 25-41, May 20, 2015.
Igor Yu Goryshin et al., Tn5 in Vitro Transposition, The Journal of Biological Chemistry, vol. 273, No. 13, pp. 7367-7374, 1998.
Norberto B. De La Cruz et al., Characterization of the Tn5 Transposase and Inhibitor Proteins: a Model for the Inhibition of Transposition, Journal of Bacteriology, vol. 175, No. 21, pp. 6932-6938, 1993.
Examiner's Communication and Report dated Mar. 31, 2022 in counterpart European Application No. 16728718.4.
Klastner P R er al., "Stabilized, freeze-dried PCR mix for detection of mycobacteria", Journal of Clinical Microbiology, vol. 36, No. 6, Jun. 1, 1998, pp. 1798-1800.

\* cited by examiner

*Primary Examiner* — Jennifer Dunston
(74) *Attorney, Agent, or Firm* — McNeill Baur PLLC

(57) ABSTRACT

Presented herein are methods and compositions surface-based tagmentation. In particular embodiments, methods of preparing an immobilized library of fragmented and tagged DNA molecules on a solid surface are presented. In particular embodiments, the solid surface comprises immobilized transposomes in a dried format, suitable for reconstitution upon contact with liquid, such as a liquid sample.

16 Claims, 29 Drawing Sheets

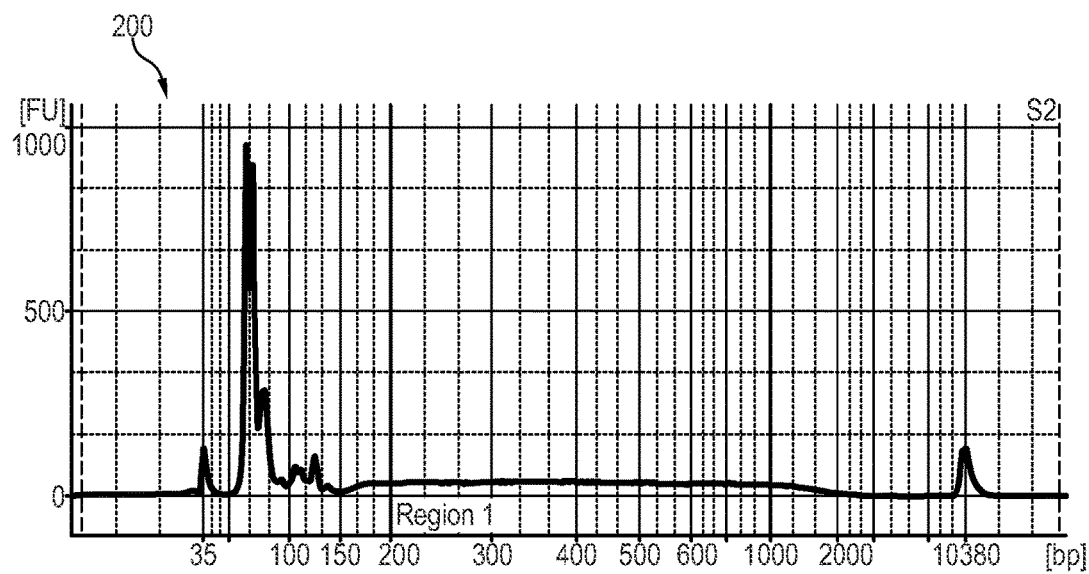
Fig. 2A
Fig. 2B
| Sample | Yield (Mb) | Clusters (raw) | Clusters (PF) | 1st Cycle Int (PF) | % int after 20 cycles (PF) | % PF Clusters | % Align (PF) | % Mismatch Rate (PF) |
|---|---|---|---|---|---|---|---|---|
| R1 | 627640 | 1,153,198 | 726,436 | 125.9 | 97.1 | 62.99 | 94.37 | 0.05 |
| R2 | 627640 | 1,153,198 | 726,436 | 161.9 | 92.8 | 62.99 | 91.29 | 0.41 |
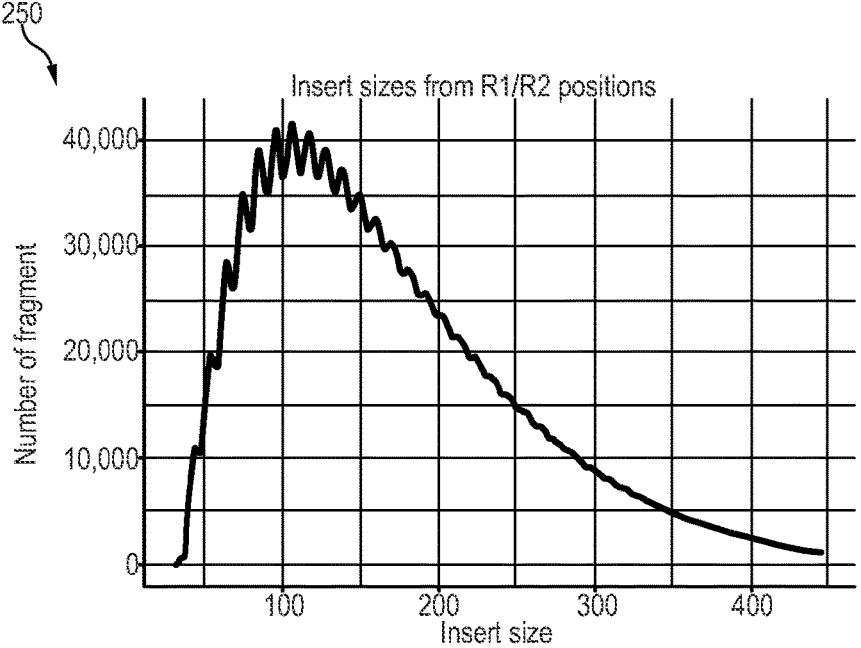
Fig. 2C

| Sample | Sample Yield (Mbases) | Clusters (raw) | Clusters (PF) | 1st Cycle Int (PF) | % intensity after 20 cycles (PF) | % PF Clusters | % Align PF | % Mismatch Rate (PF) | %>=Q30 bases (PF) |
|---|---|---|---|---|---|---|---|---|---|
| Read 1 | 571865 | 768762 | 661881 | 134.2 | 102 | 86.1 | 88.97 | 0.28 | 96.7 |
| Read 2 | 571865 | 768762 | 661881 | 168.9 | 99.5 | 86.1 | 87.27 | 0.46 | 91 |

| Sample | Sample Yield (Mbases) | Clusters (raw) | Clusters (PF) | 1st Cycle Int (PF) | % intensity after 20 cycles (PF) | % PF Clusters | % Align (PF) | % Mismatch Rate (PF) | %>=Q30 bases (PF) |
|---|---|---|---|---|---|---|---|---|---|
| Read 1 | 618531 | 842549 | 715894± | 177.8 | 100.4 | 84.97 | 69.77 | 0.31 | 96.7 |
| Read 2 | 618531 | 842549 | 715894 | 166.4 | 97.4 | 84.97 | 69.11 | 0.5 | 78.7 |

| Sample | Sample Yield (Mbases) | Clusters (raw) | Clusters (PF) | 1st Cycle Int (PF) | % intensity after 20 cycles (PF) | % PF Clusters | % Align (PF) | % Mismatch Rate (PF) |
|---|---|---|---|---|---|---|---|---|
| Read 1 | 284888 | 345775 | 329732 | 38.3 | 135.6 | 95.36 | 95.96 | 0.02 ± 0.00 |
| Read 2 | 284888 | 345775 | 329732 | 52.1 | 136.6 | 95.36 | 95.44 | 0.05 |

1000

| Sample | Sample Yield (Mbases) | Clusters (raw) | Clusters (PF) | 1st Cycle Int (PF) | % intensity after 20 cycles (PF) | % PF Clusters | % Align (PF) | % Mismatch Rate (PF) |
|---|---|---|---|---|---|---|---|---|
| Read 1 | 68136 | 131302 | 78862 | 42.1 | 123.4 | 60.43 | 89.08 | 0.14 |
| Read 2 | 68136 | 131302 | 78862 | 51.4 | 121.3 | 60.43 | 88.78 | 0.2 |

| Sample | | No of clusters with equal volume of PCR product | | | | | | | |
|---|---|---|---|---|---|---|---|---|---|
| pM used to cluster | | 15 | | 19 | | 21 | | 24 | |
| | | K/mm2 | % | K/mm2 | % | K/mm2 | % | K/mm2 | % |
| 50 ng | | 466 | 100 | 541 | 100 | 618 | 100 | 668 | 100 |
| 250 ng | | 504 | 108 | 598 | 110 | 703 | 114 | 740 | 111 |
| 1000 ng | | 512 | 109 | 602 | 111 | 670 | 108 | 716 | 107 |
| *50ng full repeat | | 377 | 81 | 455 | 84 | 516 | 83 | 555 | 83 |

|  | Median Insert Size | Mean Insert Size |
|---|---|---|
| BBN50-index1 | 341 | 409.78 |
| BBN500-index1 | 344 | 415.89 |
| BBN50-index2 | 337 | 405.97 |
| BBN500-index2 | 346 | 419.91 |
| BBN50-index3 | 330 | 400.35 |
| BBN500-index3 | 327 | 398.65 |
| BBN50-index4 | 321 | 388.71 |
| BBN500-index4 | 328 | 400.75 |
| BBN50-index5 | 327 | 397.62 |
| BBN500-index5 | 328 | 399.88 |
| BBN50-index6 | 324 | 389.35 |
| BBN500-index6 | 331 | 401.50 |

Fig. 19

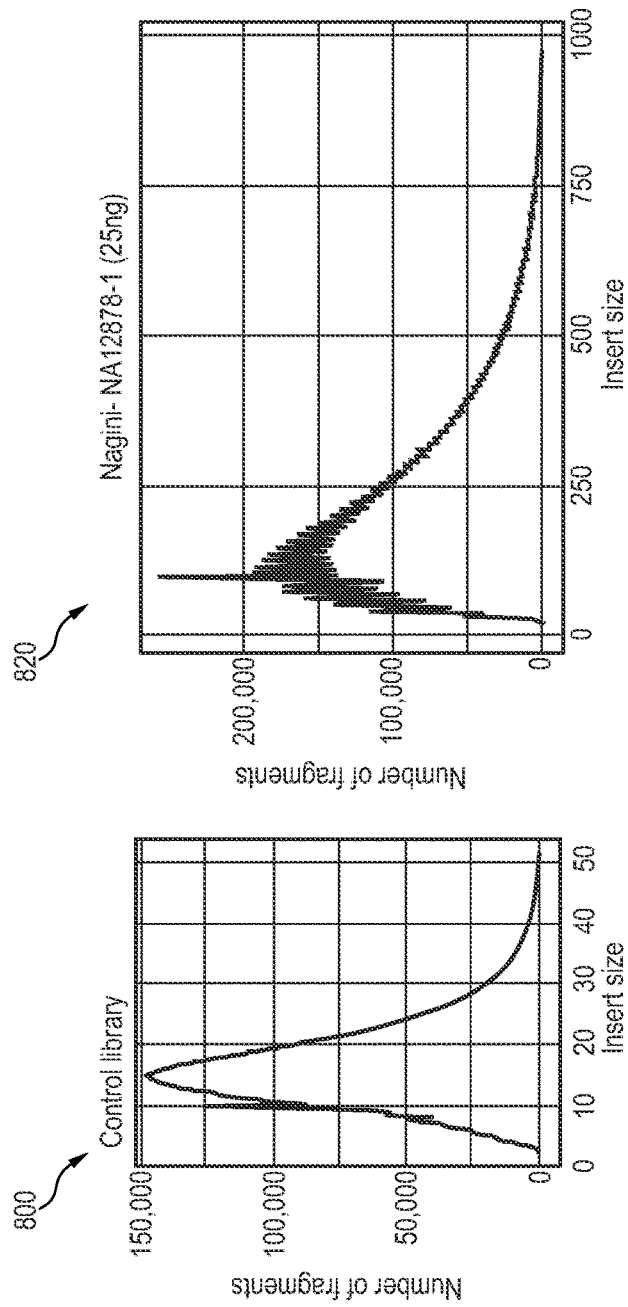

SURFACE-BASED TAGMENTATION

CROSS-REFERENCE TO RELATED APPLICATIONS

This application is a National Stage Entry of PCT/GB2016/051563, filed May 27, 2016, which claims the benefit of priority to U.S. Provisional Patent Application No. 62/167,463, filed May 28, 2015.

BACKGROUND

Sequencing methodology of next-generation sequencing (NGS) platforms typically makes use of nucleic acid fragment libraries. In one example, nucleic acid fragment libraries may be prepared using a transposon-based method, such as Illumina's Nextera™ technology. In this example, free transposon ends and a modified transposase are used to form a transposome complex. The transposome complex is then used to fragment and tag the nucleic acid generating a sequencer-ready tagmented library. However, in a standard solution-based tagmentation reaction it may be difficult to produce a uniform fragment size and library yield. Further, it is often necessary to purify the tagmentation products prior to polymerase chain reaction (PCR) amplification. Therefore, there is a need for improved tagmentation methods that provide for uniform fragment size and library yield, and streamlines the tagmentation workflow.

BRIEF SUMMARY

Presented herein are methods and compositions surface-based tagmentation. In particular embodiments, methods of preparing an immobilized library of fragmented and tagged DNA molecules on a solid surface are presented. In particular embodiments, the solid surface comprises immobilized transposomes in a dried format, suitable for reconstitution upon contact with liquid, such as a liquid sample.

Accordingly, one embodiment presented herein is a method of preparing a solid support for DNA amplification comprising: (a) providing a solid support having transposome complexes immobilized thereon; (b) applying a target nucleic acid to the solid support under conditions suitable for tagmentation, thereby immobilizing fragments of the target nucleic acid to the solid support; (c) washing the solid support to remove any unbound nucleic acids; and (d) amplifying the immobilized fragments.

Also presented is a lateral flow device for tagmentation comprising a solid support comprising: a sample deposition region; a buffer region; and a tagmentation region comprising immobilized transposome complexes; wherein the solid support is configured for sample migration via capillary action from the sample deposition region to the tagmentation region.

Also presented is method for sample preparation comprising: (a) providing a lateral flow device according to claim 9; and (b) applying a liquid sample to the sample deposition region; wherein the liquid sample migrates via capillary action from the sample deposition region to the tagmentation region and nucleic acid in the liquid sample is tagmented and immobilized by the immobilized transposomes.

Also presented is a swab comprising an absorbent capture material with lysis reagents and tagmentation reagents contained thereon.

Also presented is a method of transposome-mediated tagmentation of single-stranded target nucleic acids comprising: (a) applying a single-stranded nucleic acid to a solid support comprising an immobilized capture sequence under conditions whereby the single-stranded nucleic acid hybridizes to the capture sequence; (b) extending the immobilized capture sequence to obtain a double-stranded nucleic acid; (c) applying a transposome complex to the solid support under conditions suitable for tagmentation of the double-stranded nucleic acid.

The details of one or more embodiments are set forth in the accompanying drawings and the description below. Other features, objects, and advantages will be apparent from the description and drawings, and from the claims.

BRIEF DESCRIPTION OF THE DRAWINGS

FIG. 2A shows a plot of a Bioanalyzer trace of the fragment size distribution of the tagmented DNA prepared using the method of FIG. 1;

FIG. 2B shows a data table of read 1 and read 2 sequencing metrics for a sequencing run evaluating the tagmented DNA library of FIG. 2A;

FIG. 2C shows a plot of the insert size generated from the output sequencing data for the tagmented DNA library of FIG. 2A;

FIG. 18 shows a data table of an example of the DNA yield in terms of cluster number from the bead-based tagmentation process of FIG. 17;

FIG. 19 shows a data table of another example of the reproducibility of the bead-based tagmentation process of FIG. 17 in terms of uniform size;

FIGS. 22A, 22B, and 22C show a plot of insert size in a control library, a plot of insert size in a bead-based tagmented library, and a summary data table, respectively, in the exome enrichment assay.

DETAILED DESCRIPTION

Figure 1:
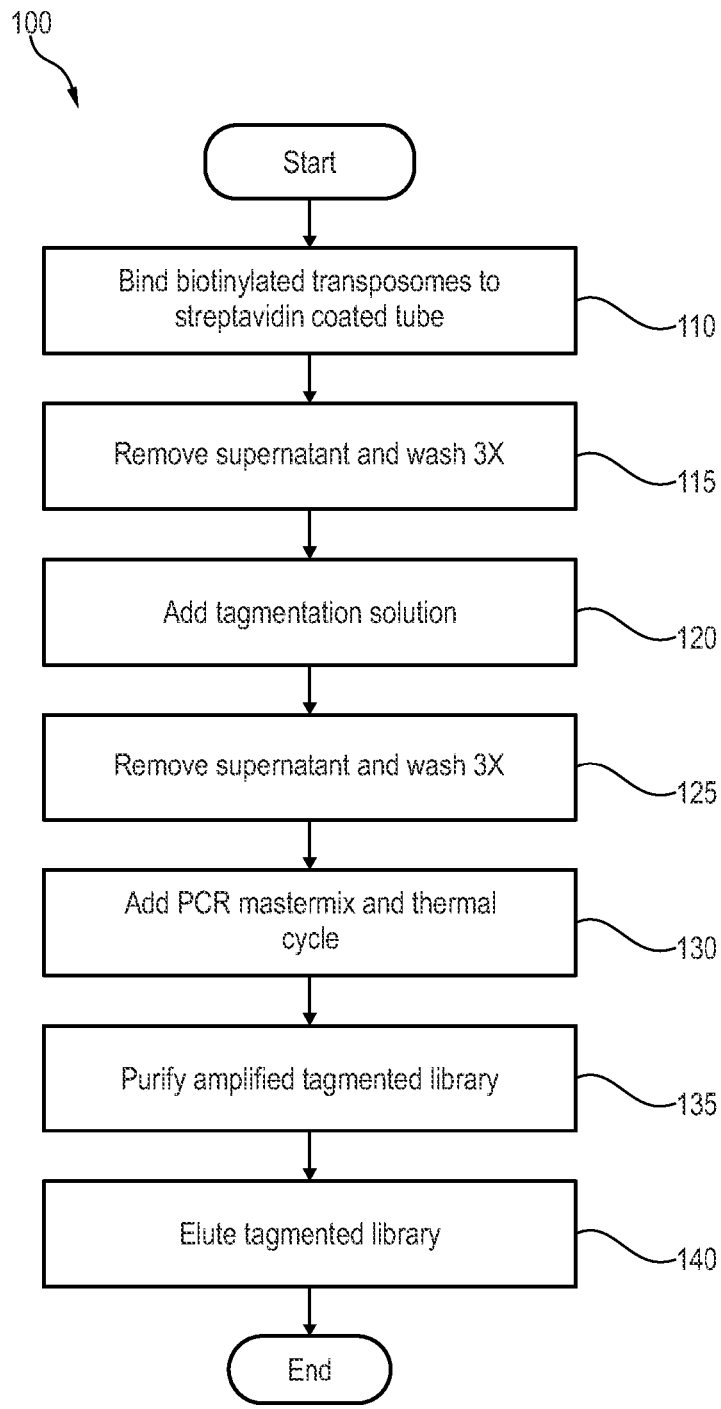
FIG. 1 is a schematic illustrating a flow diagram of an example of a method of fragmenting and tagging DNA using transposome complexes immobilized on the surface of a sample tube.

Presented herein are methods and compositions surface-based tagmentation. In particular embodiments, methods of preparing an immobilized library of fragmented and tagged DNA molecules on a solid surface are presented. In particular embodiments, the solid surface comprises immobilized transposomes in a dried format, suitable for reconstitution upon contact with liquid, such as a liquid sample.

In various embodiments, immobilization of transposomes on a solid surface provide for uniform fragment size and library yield. The density of transposomes immobilized on a solid surface may be selected to modulate fragment size and library yield.

In one embodiment, the solid surface is the inner surface of a sample tube. In one example, the sample tube is a PCR tube. In another embodiment, the solid surface is a capture membrane. In one example, the capture membrane is a biotin-capture membrane (available from Promega Corporation). In another example, the capture membrane is filter paper. Because the tagmented DNA is immobilized on a solid surface, the need to purify the tagmentation products prior to PCR amplification is obviated.

The methods according to one embodiment also provide a mechanism to standardize a tagmentation reaction. For example, immobilization of transposome complexes on a sold surface provides a fixed number of transposome complexes for the tagmentation reaction.

As used herein, the term "tagmentation" refers to the modification of DNA by a transposome complex comprising transposase enzyme complexed with adaptors comprising transposon end sequence. Tagmentation results in the simultaneous fragmentation of the DNA and ligation of the adaptors to the 5' ends of both strands of duplex fragments. Following a purification step to remove the transposase enzyme, additional sequences can be added to the ends of the adapted fragments, for example by PCR, ligation, or any other suitable methodology known to those of skill in the art.

The method of the invention can use any transposase that can accept a transposase end sequence and fragment a target nucleic acid, attaching a transferred end, but not a non-transferred end. A "transposome" is comprised of at least a transposase enzyme and a transposase recognition site. In some such systems, termed "transposomes", the transposase can form a functional complex with a transposon recognition site that is capable of catalyzing a transposition reaction. The transposase or integrase may bind to the transposase recognition site and insert the transposase recognition site into a target nucleic acid in a process sometimes termed "tagmentation". In some such insertion events, one strand of the transposase recognition site may be transferred into the target nucleic acid.

In standard sample preparation methods, each template contains an adaptor at either end of the insert and often a number of steps are required to both modify the DNA or RNA and to purify the desired products of the modification reactions. These steps are performed in solution prior to the addition of the adapted fragments to a flowcell where they are coupled to the surface by a primer extension reaction that copies the hybridized fragment onto the end of a primer covalently attached to the surface. These 'seeding' templates then give rise to monoclonal clusters of copied templates through several cycles of amplification.

The number of steps required to transform DNA into adaptor-modified templates in solution ready for cluster formation and sequencing can be minimized by the use of transposase mediated fragmentation and tagging.

In some embodiments, transposon based technology can be utilized for fragmenting DNA, for example as exemplified in the workflow for Nextera™ DNA sample preparation kits (Illumina, Inc.) wherein genomic DNA can be fragmented by an engineered transposome that simultaneously fragments and tags input DNA ("tagmentation") thereby creating a population of fragmented nucleic acid molecules which comprise unique adapter sequences at the ends of the fragments.

Some embodiments can include the use of a hyperactive Tn5 transposase and a Tn5-type transposase recognition site (Goryshin and Reznikoff, J. Biol. Chem., 273:7367 (1998)), or MuA transposase and a Mu transposase recognition site comprising R1 and R2 end sequences (Mizuuchi, K., Cell, 35: 785, 1983; Savilahti, H, et al., EMBO J., 14: 4893, 1995). An exemplary transposase recognition site that forms a complex with a hyperactive Tn5 transposase (e.g., EZ-Tn5™ Transposase, Epicentre Biotechnologies, Madison, Wis.).

More examples of transposition systems that can be used with certain embodiments provided herein include Staphylococcus aureus Tn552 (Colegio et al., J. Bacteriol., 183: 2384-8, 2001; Kirby C et al., Mol. Microbiol., 43: 173-86, 2002), Ty1 (Devine & Boeke, Nucleic Acids Res., 22: 3765-72, 1994 and International Publication WO 95/23875), Transposon Tn7 (Craig, N L, Science. 271: 1512, 1996; Craig, N L, Review in: Curr Top Microbiol Immunol., 204:27-48, 1996), Tn/O and IS10 (Kleckner N, et al., Curr Top Microbiol Immunol., 204:49-82, 1996), Mariner transposase (Lampe D J, et al., EMBO J., 15: 5470-9, 1996), Tc1 (Plasterk R H, Curr. Topics Microbiol. Immunol., 204: 125-43, 1996), P Element (Gloor, G B, Methods Mol. Biol., 260: 97-114, 2004), Tn3 (Ichikawa & Ohtsubo, J Biol. Chem. 265:18829-32, 1990), bacterial insertion sequences (Ohtsubo & Sekine, Curr. Top. Microbiol. Immunol. 204: 1-26, 1996), retroviruses (Brown, et al., Proc Natl Acad Sci USA, 86:2525-9, 1989), and retrotransposon of yeast (Boeke & Corces, Annu Rev Microbiol. 43:403-34, 1989). More examples include ISS, Tn10, Tn903, IS911, and engineered versions of transposase family enzymes (Zhang et al., (2009) PLoS Genet. 5:e1000689. Epub 2009 Oct. 16; Wilson C. et al (2007) J. Microbiol. Methods 71:332-5).

Briefly, a "transposition reaction" is a reaction wherein one or more transposons are inserted into target nucleic acids at random sites or almost random sites. Essential components in a transposition reaction are a transposase and DNA oligonucleotides that exhibit the nucleotide sequences of a transposon, including the transferred transposon sequence and its complement (i.e., the non-transferred transposon end sequence) as well as other components needed to form a functional transposition or transposome complex. The DNA oligonucleotides can further comprise additional sequences (e.g., adaptor or primer sequences) as needed or desired.

The adapters that are added to the 5' and/or 3' end of a nucleic acid can comprise a universal sequence. A universal sequence is a region of nucleotide sequence that is common to, i.e., shared by, two or more nucleic acid molecules. Optionally, the two or more nucleic acid molecules also have regions of sequence differences. Thus, for example, the 5' adapters can comprise identical or universal nucleic acid sequences and the 3' adapters can comprise identical or universal sequences. A universal sequence that may be present in different members of a plurality of nucleic acid molecules can allow the replication or amplification of multiple different sequences using a single universal primer that is complementary to the universal sequence.

Methods of Use

The transposases presented herein can be used in a sequencing procedure, such as an in vitro transposition technique. Briefly, in vitro transposition can be initiated by contacting a transposome complex and a target DNA. Exemplary transposition procedures and systems that can be readily adapted for use with the transposases of the present disclosure are described, for example, in WO 10/048605; US 2012/0301925; US 2013/0143774, each of which is incorporated herein by reference in its entirety.

For example, in some embodiments, the transposase enzymes presented herein can be used in a method for generating a library of tagged DNA fragments from target DNA comprising any dsDNA of interest (e.g., for use as next-generation sequencing or amplification templates), the method comprising: incubating the target DNA in an in vitro transposition reaction with at least one transposase and a transposon end composition with which the transposase forms a transposition complex, the transposon end composition comprising (i) a transferred strand that exhibits a transferred transposon end sequence and, optionally, an additional sequence 5'-of the transferred transposon end sequence, and (ii) a non-transferred strand that exhibits a sequence that is complementary to the transferred transposon end sequence, under conditions and for sufficient time wherein multiple insertions into the target DNA occur, each of which results in joining of a first tag comprising or consisting of the transferred strand to the 5' end of a nucleotide in the target DNA, thereby fragmenting the target DNA and generating a population of annealed 5'-tagged DNA fragments, each of which has the first tag on the 5'-end; and then joining the 3'-ends of the 5'-tagged DNA fragments to the first tag or to a second tag, thereby generating a library of tagged DNA fragments (e.g., comprising either tagged circular ssDNA fragments or 5'- and 3'-tagged DNA fragments (or "di-tagged DNA fragments")).

Tagmentation Using Transposomes Immobilized on a Sample Tube

In one embodiment, transposome complexes may be immobilized on the inner surface of a sample tube.

FIG. 1 illustrates a flow diagram of an example of a method 100 of fragmenting and tagging DNA using transposome complexes immobilized on the surface of a sample tube. Method 100 includes, but is not limited to, the following steps.

At a step 110, biotinylated transposome complexes are bound to a streptavidin coated tube. Transposome complexes comprise biotinylated oligonucleotide (adapter) sequences and transposase enzyme. In one example, both oligonucleotide (adapter) sequences are biotinylated. In another example, only one oligonucleotide (adapter) sequence is biotinylated. In one example, the streptavidin coated tube is a PCR tube. The biotinylated transposomes (e.g., 25 nM) are added to the streptavidin coated tube and incubated with shaking at room temperature for about 1 hour. The transposomes are bound to the tube surface via a biotin-streptavidin binding complex. In this example, transposome complexes are immobilized on a tube surface via a biotin-streptavidin linkage, but any suitable DNA chemistry that may be used to bind oligonucleotides to a solid surface may be used.

At a step 115, the supernatant is removed from the tube and the surface of the tube with transposomes thereon is washed three times using a wash buffer.

At a step 120, a tagmentation solution is added to the tube and incubated at 55° C. for about 15 minutes. The tagmentation solution comprises DNA (e.g., about 50 ng of DNA or about 100 ng of DNA) and a tagmentation buffer. In one example, the tagmentation buffer is the Nextera tagmentation buffer. When the solution of DNA is added to the bound transposomes, tagmentation occurs linking the DNA to the surface of the tube. An immobilized library of tagged DNA fragments is generated.

At a step 125, the supernatant is removed from the tube and the surface of the tube that has the tagmented DNA thereon is washed three times using a wash buffer. Because the tagmented DNA is immobilized on the surface of the tube, one or more wash steps (or no wash steps) are sufficient to remove the tagmentation reagents from the immobilized tagmented DNA sample and additional purification steps (e.g., SPRI bead clean-up or Zymo purification column) are obviated.

At a step 130, a solution of PCR reagents (mastermix) is added to the tube and the tagmented DNA is amplified by thermal cycling (e.g., 5 thermal cycles). Amplification liberates copies of the tagmentation products form the surface of the tube.

At a step 135, the supernatant that includes the amplified tagmented DNA is removed from the tube and the DNA is purified. In one example, the amplified tagmented DNA is purified using a Zymo spin column (available from Zymo Research, Irvine Calif.).

At a step 140, the purified tagmented DNA is eluted from the purification column using 12 µL of elution buffer. The tagmented DNA library is now ready for sequencing.

FIG. 2A shows a plot 200 of a Bioanalyzer trace of the fragment size distribution of the tagmented DNA prepared using method 100 of FIG. 1. In this example, a commercially available streptavidin-coated PCR tube was used. The concentration of biotinylated transposomes added to the tube was 25 nM. The tagmentation solution was 100 ng of E. coli DNA in a tagmentation buffer (i.e., Nextera tagmentation buffer). An aliquot of the tagmented library was run on an Agilent Bioanalyzer chip to evaluate the fragment size distribution in the library. The data show that the library yield is relatively low. To further evaluate the tagmented library, the library was sequenced on the MiSeq system using 36 cycles of paired-end sequencing on a MiSeq instrument as described with reference to FIGS. 2B and 2C.

FIG. 2B shows a data table 225 of read 1 and read 2 sequencing metrics for a sequencing run evaluating the tagmented DNA library of FIG. 2A. The data show that for read 1 and read 2, clusters that pass filter (% PF Clusters) is about 63%. When clusters are analyzed, the least reliable data (often derived from overlapping clusters) is removed from the analysis results. Therefore, the raw data is filtered to remove any reads that do not meet the overall quality as measured by a chastity filter. The chastity of a base call is calculated as the ratio of the brightest intensity divided by the sum of the brightest and second brightest intensities. For example, clusters "pass filter (PF)" if no more than one base call in the first 25 cycles has a chastity of <0.6. The data also show that the percentage of clusters (PF) that align to the reference genome is about 94% in read 1 and about 91% in read 2.

FIG. 2C shows a plot 250 of the insert size generated from the output sequencing data for the tagmented DNA library of FIG. 2A. The data show that the library insert size is about 170 bp.

The diversity (not shown) of the tagmented library was about 44M. The diversity is the number of unique molecules in the library and is used as an indication of library complexity. The yield (not shown) was about 0.6 G.

To evaluate the effect of the streptavidin coating concentration on library yield, two sets of customized tubes that have higher concentrations of streptavidin coatings were obtained from Biomat (Rovereto, Italy). The two sets of tubes (i.e., SA1157 and SA1158) were used for the preparation of tagmented libraries using method 100 of FIG. 1. In this example, the concentration of biotinylated transposomes added to each tube was 25 nM. The tagmentation solution was 100 ng of human genomic DNA (NA12878) in a tagmentation buffer. The experimental design is shown in Table 1. Samples S1 through S4 were prepared using tube set SA1157. Samples S5 through S8 were prepared using tube set SA1158.

TABLE 1

Experimental design

| Sample | [Transposome] | DNA (NA12878) |
|---|---|---|
| S1 | 25 nM | 100 ng |
| S2 | 25 nM | 100 ng |
| S3 | 25 nM | none |
| S4 | none | none |
| S5 | 25 nM | 100 ng |
| S6 | 25 nM | 100 ng |
| S7 | 25 nM | none |
| S8 | none | none |

Figure 3:
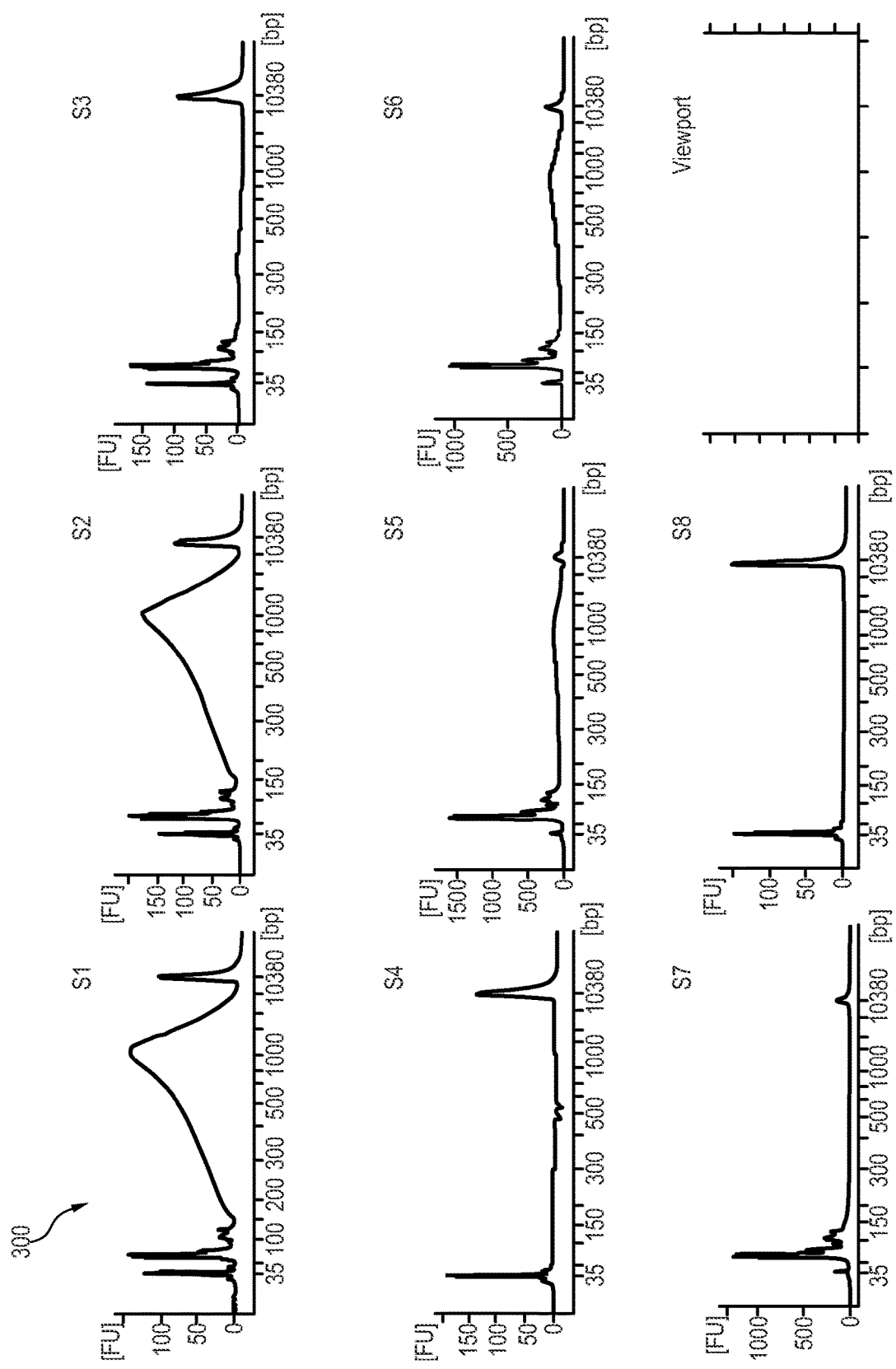
FIG. 3 shows a panel of Bioanalyzer traces of the fragment size distribution in the tagmented libraries prepared in SA1157 and SA1158 tubes.

FIG. 3 shows a panel 300 of Bioanalyzer traces of the fragment size distribution in the tagmented libraries prepared in SA1157 and SA1158 tubes. The data show that there was a significant increase in library yield in tagmented libraries (samples S1 and S2) prepared using the SA1157 tube set relative to tagmented libraries (samples S5 and S6) prepared using the SA1158 tube set. The S1 and S5 libraries were sequenced on the MiSeq system as described with reference to FIGS. 4A and 4B, and FIGS. 5A and 5B, respectively.

Figures 4A, 4B:
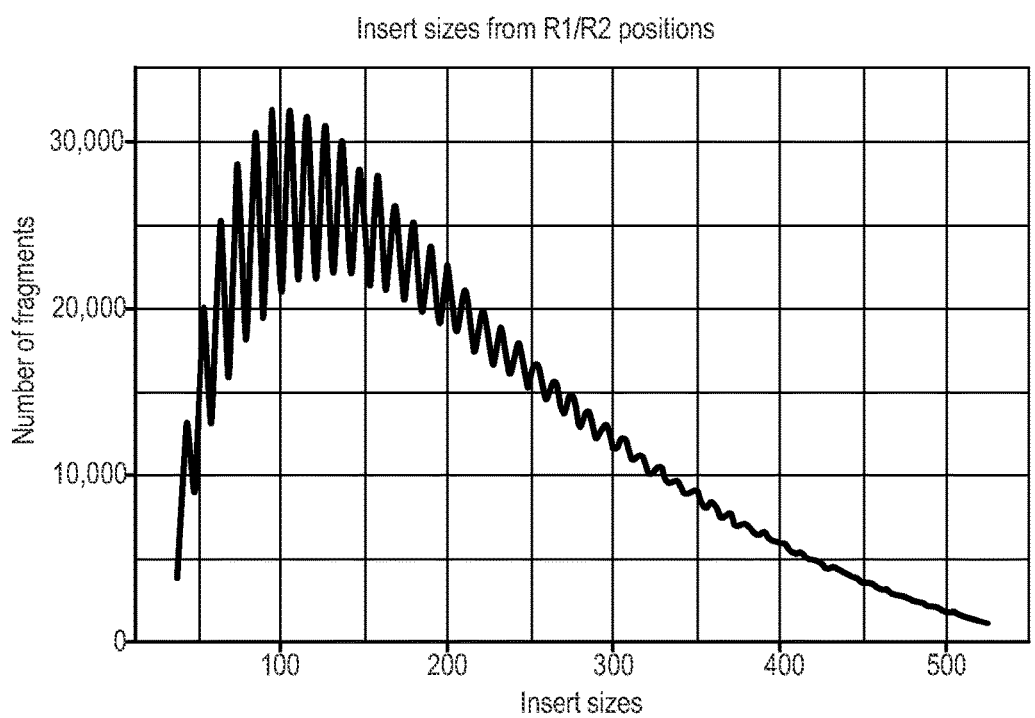
FIGS. 4A and 4B show a data table and a plot, respectively, of examples of sequencing metrics for the S1 tagmented library of FIG. 3.

FIGS. 4A and 4B show a data table 400 and a plot 450, respectively, of examples of sequencing metrics for the S1 tagmented library of FIG. 3. In this example, the S1 library was seeded onto the flow cell at a concentration of 7 pM. Referring to FIG. 4A, the data show that for read 1 and read 2, clusters that pass filter (% PF Clusters) is about 86%. The percentage of clusters passing filter that align (% Align (PF)) to the reference genome is about 89% in read 1 and about 87% in read 2. The cluster density (not shown) is 1195 K/mm2 of flow cell surface. The library diversity (not shown) is about 1.6 billion. Referring to FIG. 4B, the insert size generated from the output sequencing data for the S1 tagmented DNA library is about 181 bp.

Figures 5A, 5B:
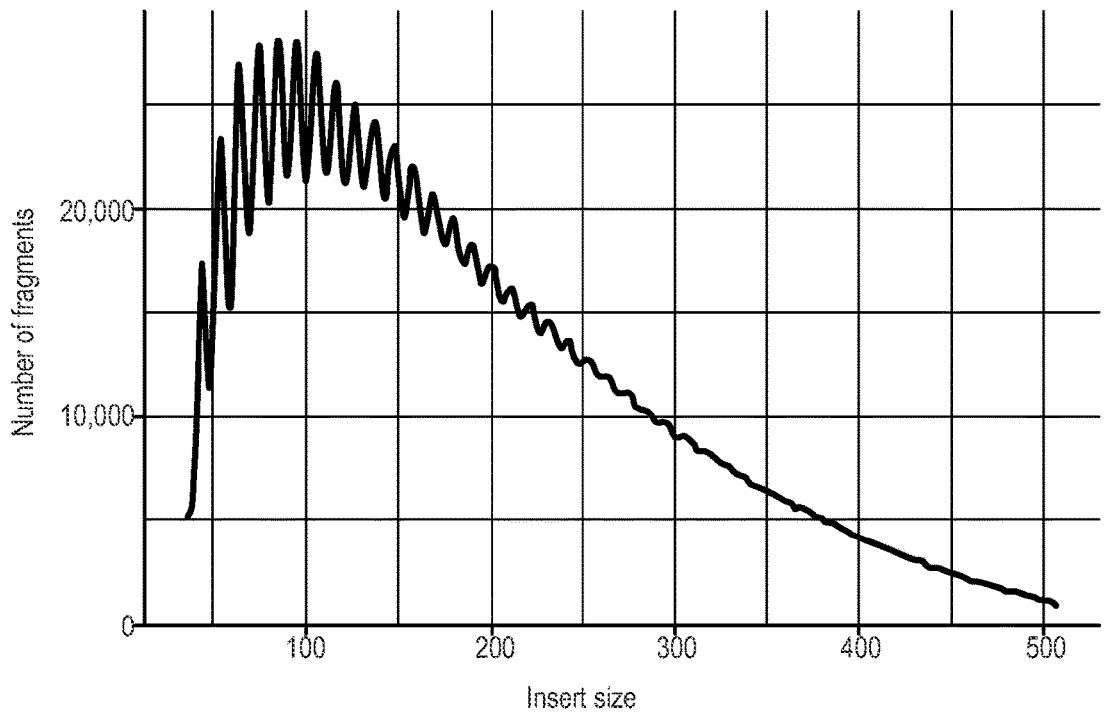
FIGS. 5A and 5B show a data table and a plot, respectively, of examples of sequencing metrics for the S5 tagmented library of FIG. 3.

FIGS. 5A and 5B show a data table 500 and a plot 550, respectively, of examples of sequencing metrics for the S5 tagmented library of FIG. 3. In this example, the S5 library was seeded onto the flow cell at a concentration of 4 pM. Referring to FIG. 5A, the data show that for read 1 and read 2, clusters that pass filter (% PF Clusters) is about 85%. The percentage of clusters passing filter that align (% Align (PF)) to the reference genome is about 69% in read 1 and read 2. The cluster density (not shown) is 1269 K/mm2 of flow cell surface. The library diversity (not shown) is about 1.5 billion. Referring to FIG. 5B, the insert size generated from the output sequencing data for the S5 tagmented DNA library is about 167 bp.

In another embodiment, the tagmentation reagents (e.g., transposome complexes and tagmentation buffer) may be dried on the inner surface of a sample tube. The suitability of dry reagent storage for various molecular assays, such as reagent components for nucleic acid assays, has been well established. Existing technologies for drying reagent liquids on a solid surface may be selected and adapted for use with transposome complexes. In one example, a reagent drying technology may be selected for efficient recovery (reconstitution) of transposome activity. In another example, reagent stabilization and/or protection compounds may be selected such that they do not substantially interfere with the tagmentation process. In yet another example, a reagent drying technology may be selected for long term stability (shelf-life) at different environmental conditions (e.g., shipping temperatures, humidity, etc).

The dried reagents may be reconstituted by the addition of a sample liquid. In one example, the sample liquid may be a relatively unpurified DNA sample, such as an impure cell lysate. In another example, the sample liquid may be a relatively pure sample, such as purified genomic DNA. When the sample solution is added to the tube, the dried tagmentation reagents (e.g., transposomes and tagmentation buffer) are reconstituted and tagmentation occurs linking the DNA to the surface of the tube.

In another embodiment, a sample tube that has dry tagmentation reagents (e.g., transposome complexes and tagmentation buffer) may include a barcode affixed on the outer surface of the tube. A barcode may be defined as an optical machine-readable representation of data relating to the object to which it is attached. A barcode may be, for example, a linear or one-dimensional (1D) code or a rectangle, dots, hexagons, and/or other geometric patterns in two dimensions (2D). Barcodes may be read by optical scanners called barcode readers or scanned from an image by special software. The barcode may be used to associate the sample with a tagmented DNA library prepared from the sample.

In one example, a barcoded sample tube that has dry tagmentation reagents thereon may be used to collect and tagment a sample at a first location. The sample liquid may then be removed from the sample tube and the tagmented DNA library sent to a second location (e.g., a central testing laboratory) for subsequent rehydration, amplification and sequencing. The barcode may be used to track the sample from the sample collection point through the sample endpoint analysis.

Tagmentation Using Transposomes Immobilized on a Capture Membrane

In another embodiment, one or more sample processing reagents, e.g., tagmentation reagents and/or sample lysing reagents, may be immobilized on a capture membrane.

Figure 6:
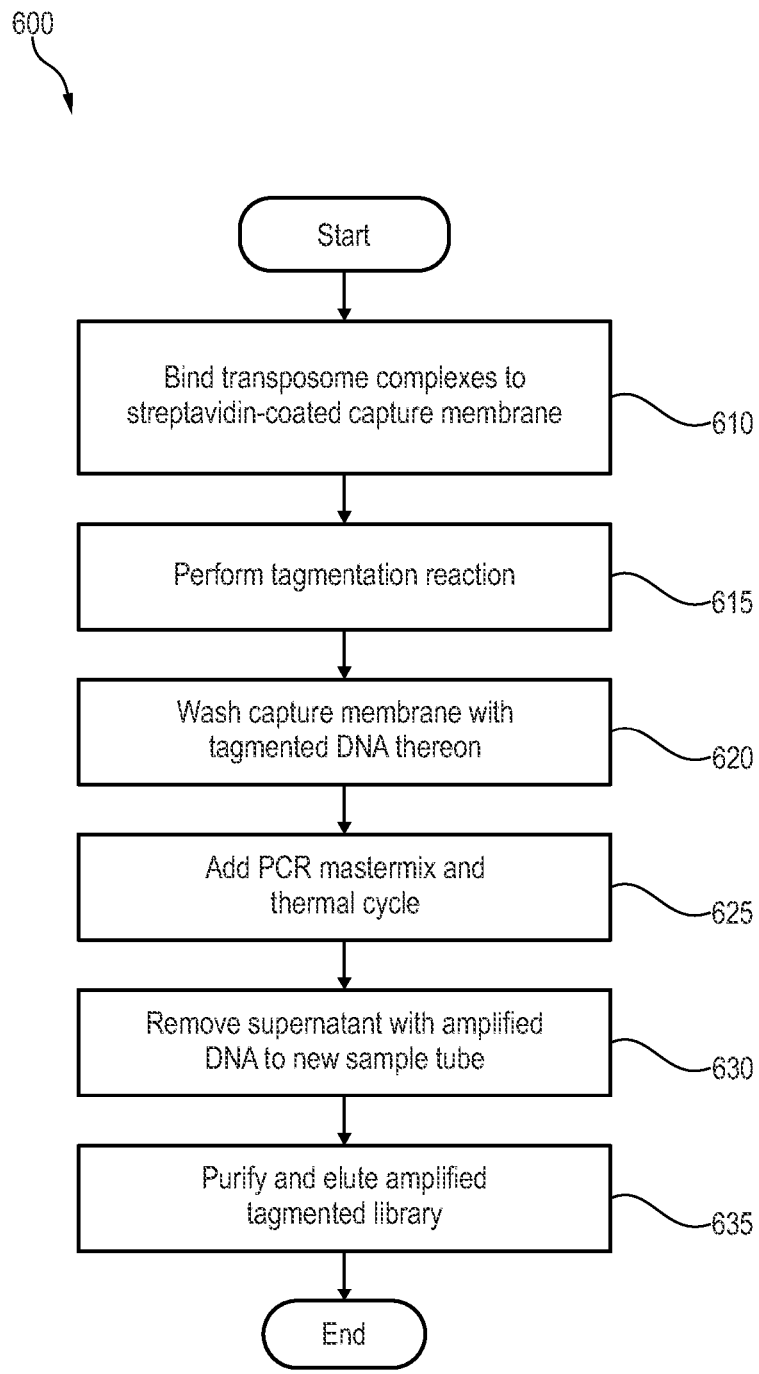
FIG. 6 illustrates a flow diagram of an example of a method of fragmenting and tagging DNA using transposome complexes immobilized on a capture membrane.
Figure 7:
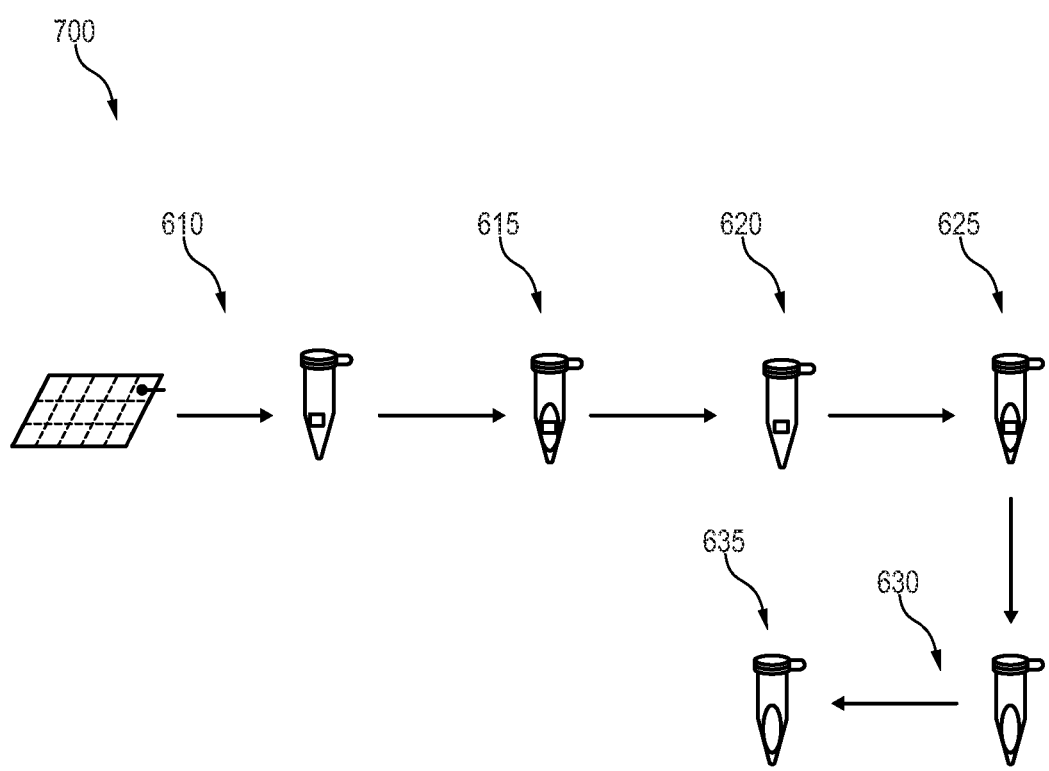
FIG. 7 illustrates a schematic diagram showing pictorially the steps of the method of FIG. 6.

FIG. 6 illustrates a flow diagram of an example of a method 600 of fragmenting and tagging DNA using transposome complexes immobilized on a capture membrane. FIG. 7 illustrates a schematic diagram 700 showing pictorially the steps of method 600 of FIG. 6. Referring now to FIG. 6, method 600 includes, but is not limited to, the following steps.

At a step 610, transposome complexes are bound to a streptavidin-coated capture membrane. For example, a piece of streptavidin-coated capture membrane is cut from a sheet and placed in a sample tube (e.g., a PCR tube). In one example, the streptavidin-coated capture membrane is a square of SAM2® Biotin Capture Membrane available from Promega (Madison, Wis.). A solution of biotinylated transposome complexes are added to the sample tube that has the streptavidin-coated capture membrane therein. Transposome complexes comprise biotinylated oligonucleotide sequences and transposase enzyme. The biotinylated transposomes (e.g., 100 nM or 50 nM) are added to the sample tube that has the streptavidin-coated capture membrane therein and incubated at room temperature for about 2 minutes. The transposomes are bound to the capture membrane via a biotin-streptavidin binding complex. After the incubation period, the supernatant is removed from the sample tube and the streptavidin-coated capture membrane with bound transposomes thereon is washed three times using a wash buffer. This step is also shown pictorially in schematic diagram 700 of FIG. 7.

At a step 615, tagmentation is performed. For example, a tagmentation solution is added to the sample tube and incubated at 55° C. for about 15 minutes. The tagmentation solution comprises DNA (e.g., about 50 ng of DNA) and a tagmentation buffer. In one example, the tagmentation buffer is the Nextera tagmentation buffer. When the solution of DNA is added to the bound transposomes, tagmentation occurs linking the DNA to the surface of streptavidin-coated capture membrane. An immobilized library of tagged DNA fragments is generated. This step is also shown pictorially in schematic diagram 700 of FIG. 7.

At a step 620, the supernatant is removed from the sample tube and the streptavidin-coated capture membrane that has tagmented DNA thereon is washed three times using a wash buffer. The wash buffer supernatant is removed and the capture membrane is retained in the sample tube. This step is also shown pictorially in schematic diagram 700 of FIG. 7.

At a step 625, a solution of PCR reagents (mastermix) is added to the sample tube and the tagmented DNA bound to the capture membrane is amplified by thermal cycling (e.g., 5 thermal cycles). Amplification liberates copies of the tagmentation products form the capture membrane. This step is also shown pictorially in schematic diagram 700 of FIG. 7.

At a step 630, the supernatant that includes the amplified tagmented DNA is removed from the sample tube and transferred to a new sample tube. The capture membrane with tagmented DNA thereon may be saved for subsequent use. This step is also shown pictorially in schematic diagram 700 of FIG. 7.

At a step 635, the amplified tagmented DNA is purified using, for example, a purification column (e.g., a Zymo spin column) and eluted. The tagmented DNA library is now ready for sequencing. This step is also shown pictorially in schematic diagram 700 of FIG. 7.

Figure 8A:
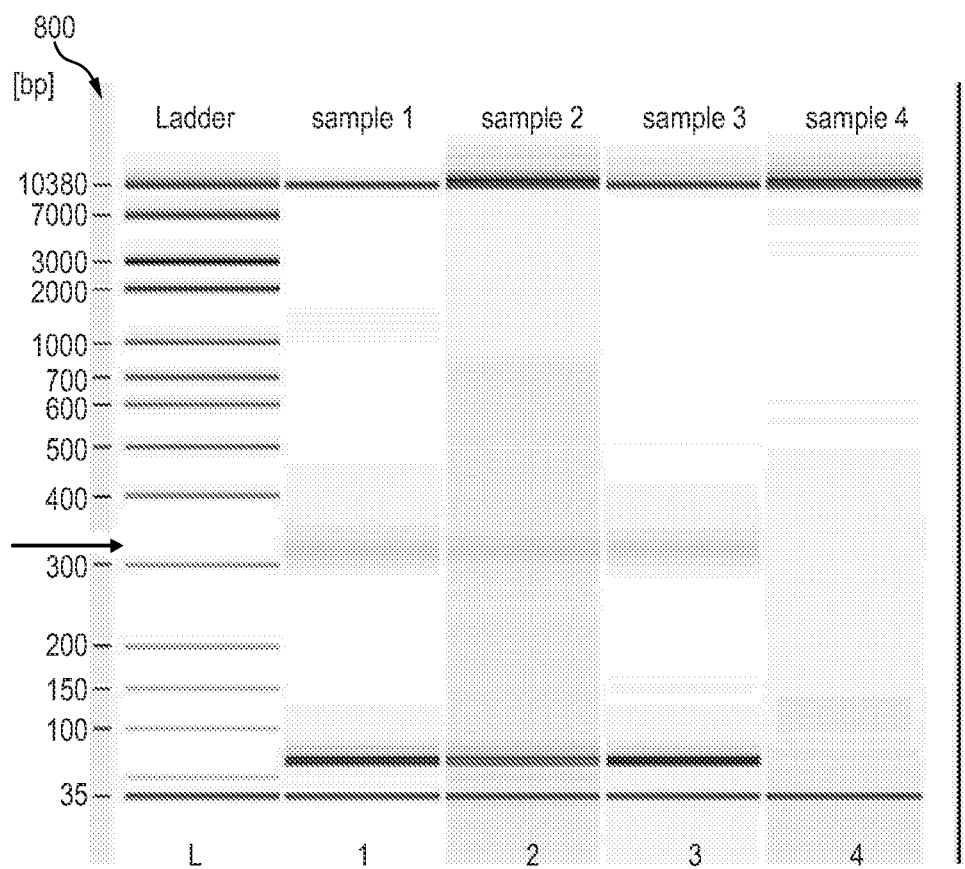
FIG. 8A shows a densitometry plot of the fragment size distributions in the tagmented DNA libraries prepared using the method of FIG. 6.
Figure 8B:
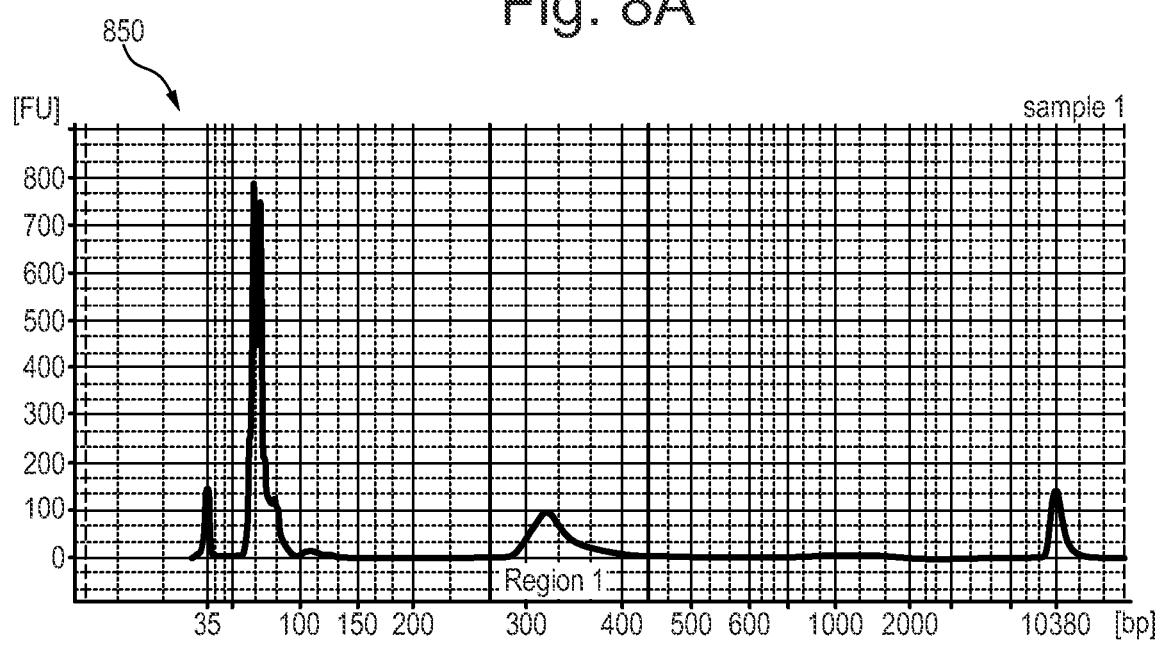
FIG. 8B shows a plot of the Bioanalyzer trace of the fragment size distribution in the S1 library of FIG. 8A.

FIG. 8A shows a densitometry plot 800 of the fragment size distributions in the tagmented DNA libraries prepared using method 600 of FIG. 6. FIG. 8B shows a plot 850 of the Bioanalyzer trace of the fragment size distribution in the S1 library of FIG. 8A. In this example, SAM2® Biotin Capture Membranes were used. The experimental design is shown in Table 2. For sample 1 (S1), the concentration of biotinylated transposomes was 100 nM. For samples S2 and S3, the concentration of biotinylated transposomes was 50 nM. *E. coli* DNA (50 ng) in tagmentation buffer (i.e., Nextera tagmentation buffer) was added only to samples S1 and S2. Sample S3 is a no-DNA control sample. An aliquot of each sample was run on an Agilent Bioanalyzer chip to evaluate the distribution of fragments sizes in the libraries.

TABLE 2

| Experimental design | | |
|---|---|---|
| Sample | [Transposome] | DNA (*E. coli*) |
| S1 | 100 nM | 50 ng |
| S2 | 50 nM | 50 ng |
| S3 | 50 nM | none |

Referring to FIGS. 8A (arrow) and 8B, the data show that the S1 and S2 libraries have an average insert size of around 350 bp. Note, a band at about 350 bp (arrow) is also observed in the no-DNA control sample S3.

To further evaluate the tagmented library, the S1, S2, and S3 samples were sequenced on the MiSeq system using 36 cycles of paired-end sequencing. The results for sample S1 are described with reference to FIGS. 9A and 9B. The results for sample S2 are described with reference to FIGS. 10A and 10B. No sequence data was obtained from sample S3.

Figures 9A, 9B:
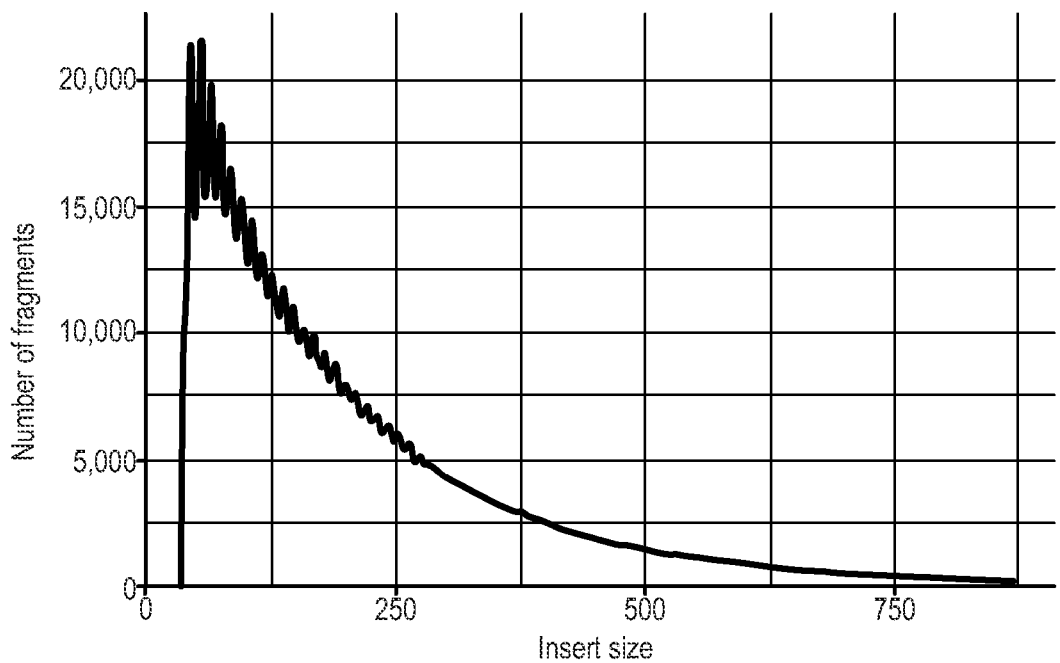
FIGS. 9A and 9B show a data table and a plot, respectively, of examples of sequencing metrics for the S1 tagmented library of FIGS. 8A and 8B.

FIGS. 9A and 9B show a data table 900 and a plot 950, respectively, of examples of sequencing metrics for the S1 tagmented library of FIGS. 8A and 8B. In this example, the S1 library was seeded onto the flow cell at a concentration of 12 pM. Referring to FIG. 9A, the data show that for read 1 and read 2, clusters that pass filter (% PF Clusters) is about 95%. The percentage of clusters passing filter that align (% Align (PF)) to the reference genome is about 96% in read 1 and 95% in read 2. The cluster density (not shown) is 504 K/mm2 of flow cell surface. The library diversity (not shown) is about 26.9 million. Referring to FIG. 9B, the insert size generated from the output sequencing data for the S1 tagmented DNA library is about 159 bp.

Figures 10A, 10B:
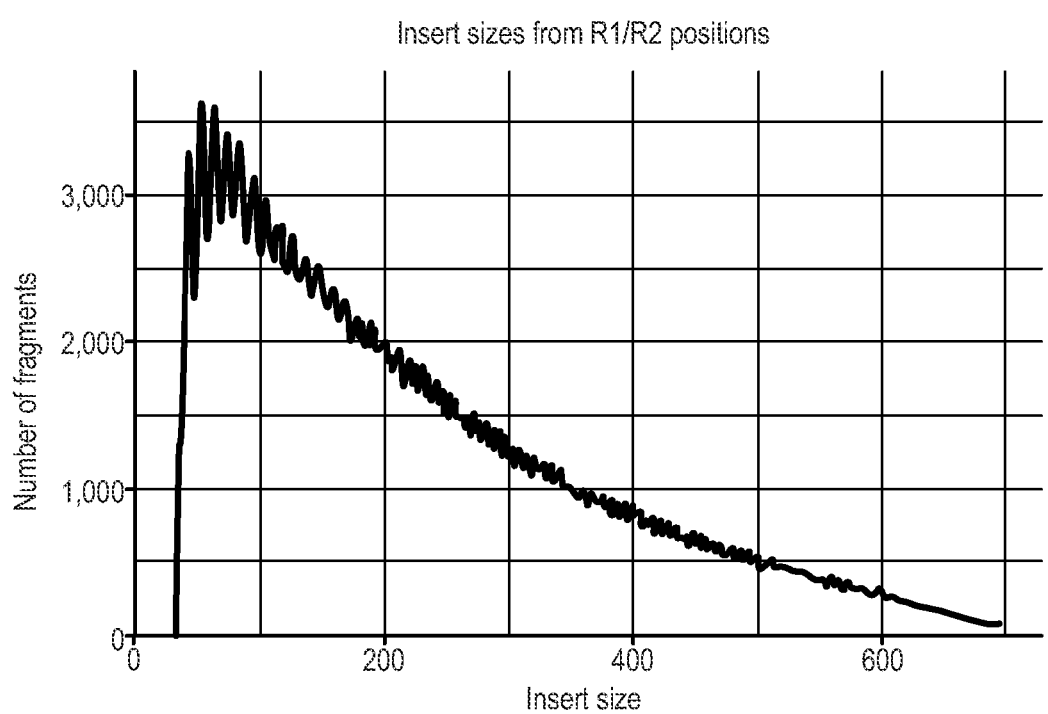
FIGS. 10A and 10B show a data table and a plot, respectively, of examples of sequencing metrics for the S2 tagmented library of FIG. 8A.

FIGS. 10A and 10B show a data table 1000 and a plot 1050, respectively, of examples of sequencing metrics for the S2 tagmented library of FIG. 8A. In this example, the S2 library was seeded onto the flow cell. Referring to FIG. 10A, the data show that for read 1 and read 2, clusters that pass filter (% PF Clusters) is about 60%. The percentage of clusters passing filter that align (% Align (PF)) to the reference genome is about 89% in read 1 and read 2. The cluster density (not shown) is 138 K/mm2 of flow cell surface. The library diversity (not shown) is about 16 million. Referring to FIG. 9B, the insert size generated from the output sequencing data for the S2 tagmented DNA library is about 189 bp.

The S2 library was prepared using transposome complexes at 50 nM. Because of the lower concentration of transposomes used (relative to the S1 library prepared using 100 nM of transposomes), the insert size is increased, and the cluster density and percent clusters that pass filter are decreased in the S2 library relative to the S1 library.

In another example, a capture membrane may be an absorbent filter paper, such as a blood-spot card used in neonatal testing. An aliquot of a tagmentation solution (e.g., transposomes and a tagmentation buffer) may be spotted onto the absorbent filter paper sheet and dried. A small disc containing the dried transposome solution thereon be punched from the filter paper sheet using an automated or manual hole-punch and placed into a sample tube (e.g., PCR tubes). A DNA-containing sample (e.g., a lysed blood sample) may be added to the sample tube to rehydrate the dried tagmentation solution and initiate a tagmentation reaction. The tagmented DNA bound to the filter paper may then be processed for subsequent sequencing.

Figure 11:
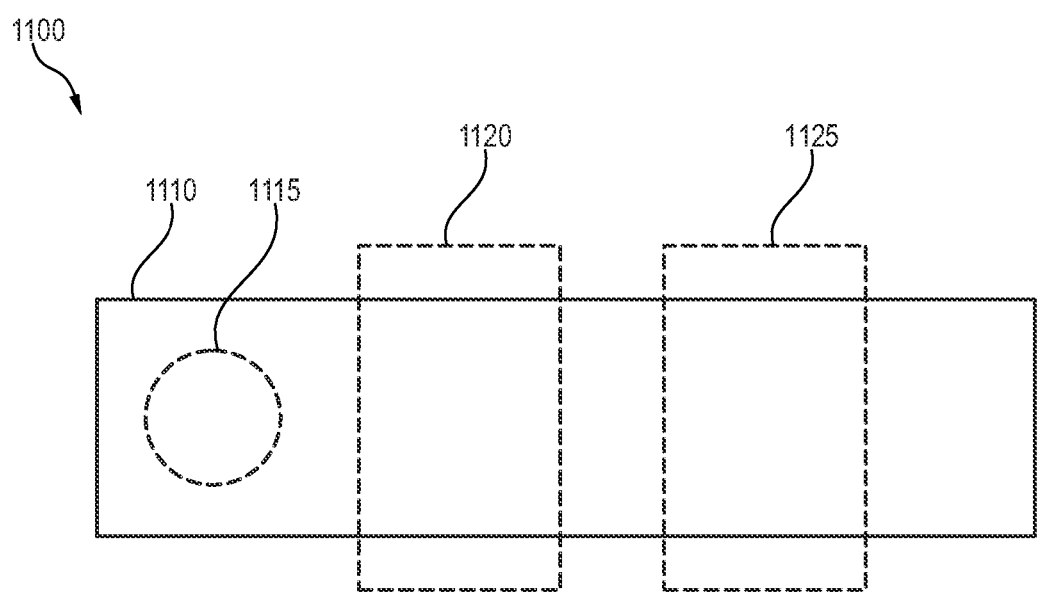
FIG. 11 illustrates a block diagram of an example of a lateral flow device for tagmentation.

In yet another example, a capture membrane may be a lateral flow device that includes different zones with immobilized reagents for tagmentation. FIG. 11 illustrates a block diagram of an example of a lateral flow device 1100 for tagmentation. Lateral flow device 1100 includes a solid support 1110. Solid support 1110 may be formed of a material through which an applied sample and/or sample components may migrate via capillary action. Solid support 1110 may include different processing zones for tagmentation of a DNA sample. For example, solid support 1110 may include a sample zone 1115, a buffer zone 1120 and a tagmentation zone 1125.

In one example, sample zone 1115 may be a zone for spotting an aliquot of a DNA-containing sample. In another example, sample zone 1115 may be a zone that may be dipped into a sample solution. A sample (not shown) applied to sample zone 1115 may migrate via capillary action to buffer zone 1120. Buffer zone 1120 may be a zone that contains, for example, dried sample buffer reagents used to lyse the sample and release DNA. As the sample migrates into buffer zone 1120, the dried sample buffer reagents are reconstituted and sample lysis occurs. The released DNA (not shown) from the lysed sample may migrate via capillary action to tagmentation zone 1125. Tagmentation zone 1125 may include dried tagmentation reagents (e.g., transposome complexes and tagmentation buffer). As the released DNA migrates into tagmentation zone 1125, the dried tagmentation reagents are reconstituted and tagmentation occurs. The tagmented DNA may then be removed from tagmentation zone 1125 for subsequent processing and sequencing. In one example, the tagmented DNA may be removed from tagmentation zone 1125 by enzymatic or chemical cleavage. In another example, the tagmented DNA may be removed from tagmentation zone 1125 by PCR amplification.

In another example, buffer zone 1120 is a zone that contains dried tagmentation buffer reagents and tagmentation zone 1125 is a zone that contains dried transposome complexes. In this example, sample zone 1115 is dipped into a DNA solution (e.g., an aqueous DNA solution).

In yet another example, a capture membrane may be a device such as a swab that comprises an absorbent capture material with lysis reagents and tagmentation reagents (e.g., transposome complexes and tagmentation buffer; Nextera reagents) contained thereon. In one example, the swab device contains fresh lysis reagents and tagmentation reagents. In another example, the swab contains dried lysis reagents and tagmentation reagents. A user may use the swab device to wipe a surface of interest to obtain a sample. As the swab device is wiped across the surface of interest, a tagmented DNA library of the sample on the surface is obtained. In one example, the swab device is a buccal swab that includes lysis reagents and tagmentation reagents (e.g., Nextera reagents). The swab device may include a barcode affixed on a surface of the swab (e.g., the swab handle). The barcode may be used to track the sample from the sample collection point through the sample endpoint analysis.

A lateral flow device as presented herein can comprise a material that facilitates the movement of fluid via capillary action. In some embodiments, the lateral flow device comprises one or more capillary beds. Capillary beds can comprise any suitable material that facilitates lateral fluid transfer. For example, in some embodiments the material comprises a porous paper. In some embodiments, the material comprises a sintered polymer, such as, for example porous plastics, microporous PTFE, porous polymeric fiber, porous glass fiber membrane, porous composites and functionalized and bioactivated porous media, and the like. Each of these elements has the capacity to transport fluid (e.g., urine, blood) spontaneously. In embodiments where the lateral flow device comprises multiple capillary beds, a first element (the sample pad) acts as a sponge and holds an excess of sample fluid. In certain embodiments, once soaked, the fluid migrates to the second element (conjugate pad) in which a dried format of buffer reagents and/or transposome complexes are situated such that, upon contact with liquid, the buffer and/or transposome complexes are reconstituted such that the reaction can take place. In certain embodiments, the transposome complexes are immobilized to the surface of the lateral flow device. In certain embodiments, the transposome complexes are embedded within a matrix of the lateral flow device. In certain embodiments, the matrix is a porous matrix. In certain embodiments, the sample fluid dissolves a dried buffer composition such as a salt-sugar matrix, and in one combined transport action the sample and buffer mix while flowing through the porous structure.

Capture and Tagmentation of Single-Stranded DNA

The invention provides a method of capturing single-stranded DNA (ssDNA) sequences on a solid surface (e.g., a flow cell surface) for construction of a tagmented library. For example, the method according to one embodiment combines a solution-based A-tailing reaction of ssDNA with a surface-bound tagmentation reaction to generate a tagmented library for sequencing. The method according to one embodiment provides a mechanism for preparing single stranded DNA molecules for sequencing. In certain applications, construction of a tagmented library from a ssDNA sample or a substantially ssDNA sample may be advantageous (e.g., construction of a tagmented library from a formalin fixed, paraffin-embedded (FFPE) sample).

Figure 12A:
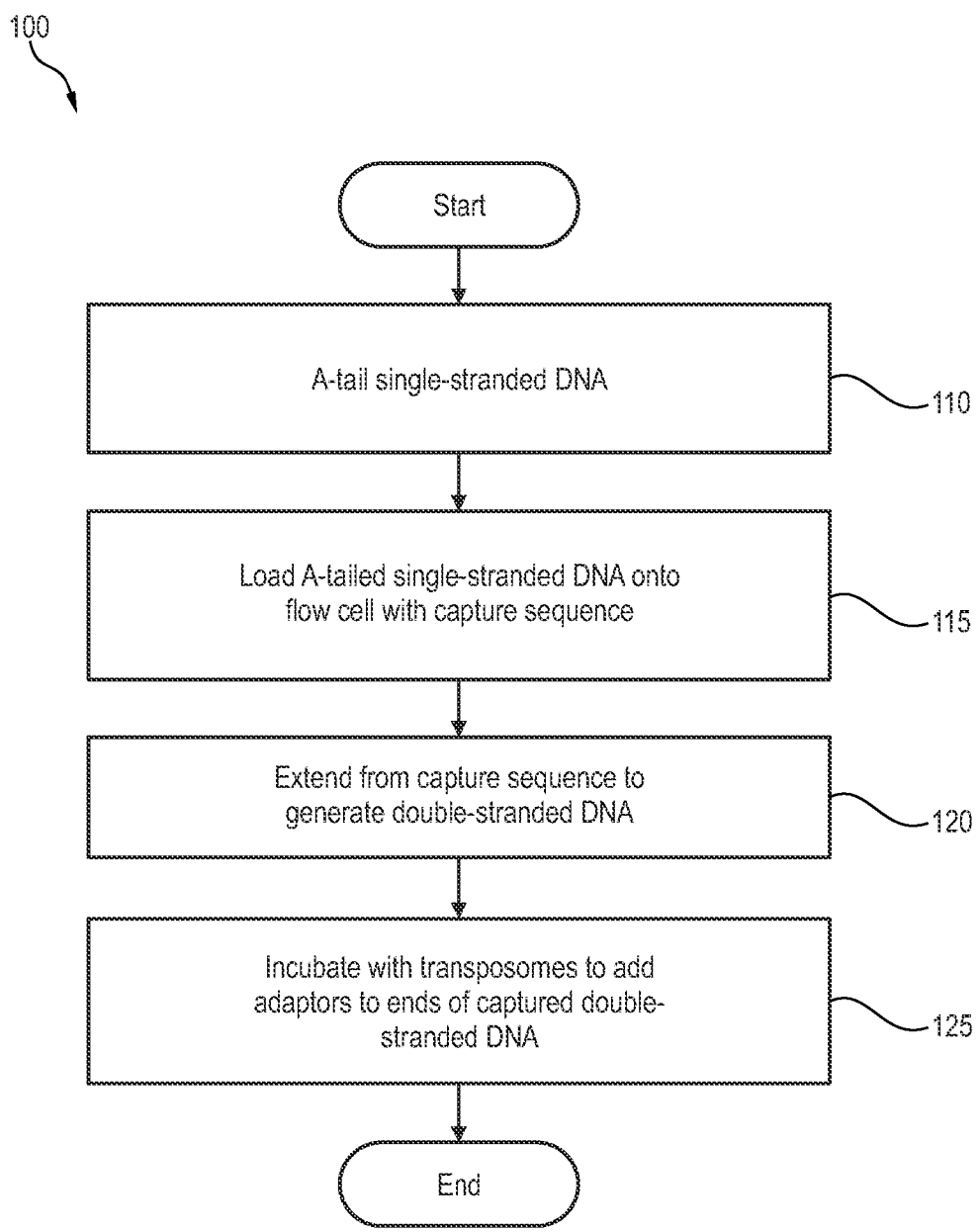
FIG. 12A illustrates a flow diagram of an example of a method of capturing ssDNA sequences on a solid surface (e.g., a flow cell surface) for construction of a tagmented library.
Figure 12B:
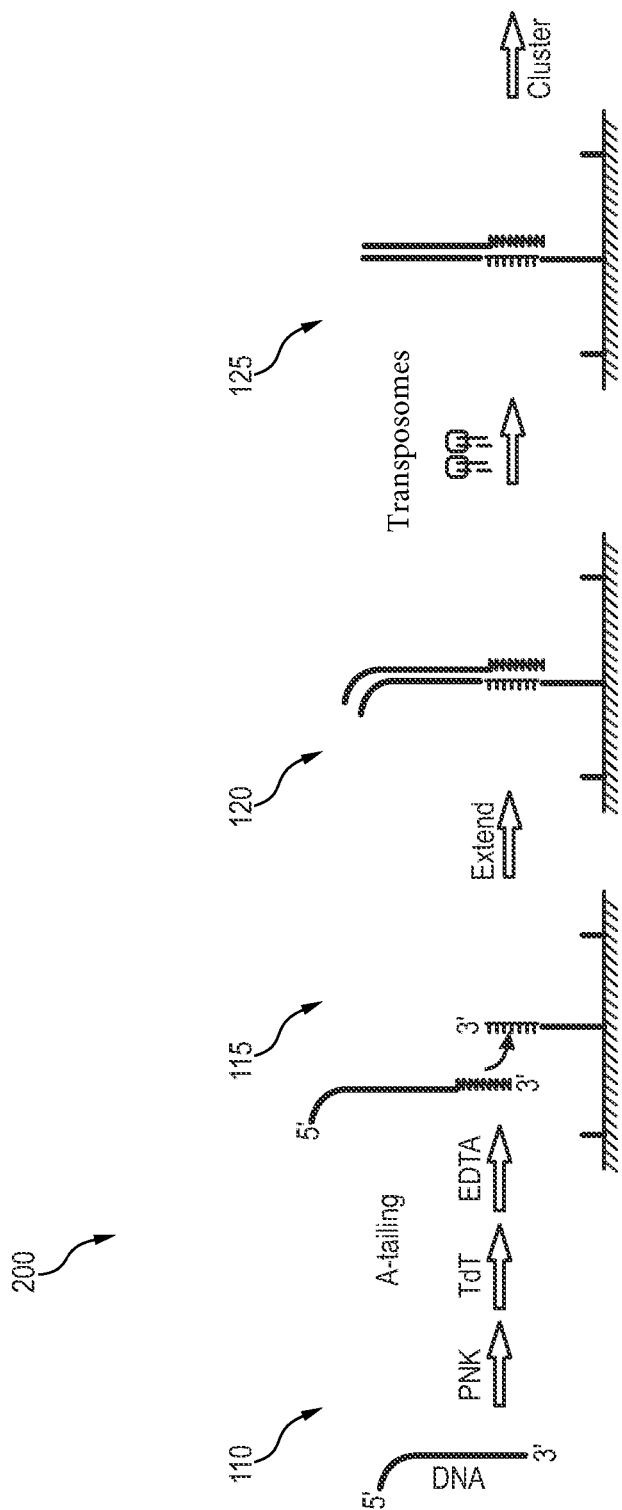
FIG. 12B illustrates a schematic diagram showing pictorially the steps of the method of FIG. 12A.

FIG. 12A illustrates a flow diagram of an example of a method 100 of capturing ssDNA sequences on a solid surface (e.g., a flow cell surface) for construction of a tagmented library. FIG. 12B illustrates a schematic diagram 200 showing pictorially the steps of method 100 of FIG. 12A. Referring now to FIG. 12A, method 100 includes, but is not limited to, the following steps.

At a step 110, a poly-A tail is added to the 3' hydroxyl terminus of a ssDNA template. The input template may be ssDNA or double-stranded DNA that has been denatured. In one example, the terminal 3'-phosphoryl groups on the ssDNA strands are first removed, e.g., using polynucleotide kinase (PNK). A poly-A tail may then be coupled to the 3'-end of the dephosphorylated molecules, e.g., using terminal transferase (TdT). This step is also shown pictorially in schematic diagram 200 of FIG. 12B.

At a step 115, the A-tailed ssDNA is loaded onto the surface of a flow cell. The surface of the flow cell includes a lawn of oligonucleotide sequences (e.g., P5 and P7) that are used for subsequent cluster amplification. On the end of one of the flow cell P5 or P7 oligonucleotide sequences is a capture sequence. The capture sequence may be a poly-T sequence that is used to capture A-tailed DNA fragments. This step is also shown pictorially in schematic diagram 200 of FIG. 12B.

At a step 120, the capture sequence is extended to generate double-stranded DNA (dsDNA). This step is also shown pictorially in schematic diagram 200 of FIG. 12B.

At a step 125, transposomes are loaded onto the flow cell to catalyze the addition of adaptors onto the ends of the dsDNA sequences. This step is also shown pictorially in schematic diagram 200 of FIG. 12B.

In another example, the capture sequence on P5 or P7 oligonucleotides may be a sequence that is complimentary to the overhang sequence of a restriction endonuclease that is used to fragment dsDNA.

In yet another example, the capture sequence on P5 or P7 oligonucleotides may be any other sequence that is complimentary to a sequence on the input DNA.

Figure 13:
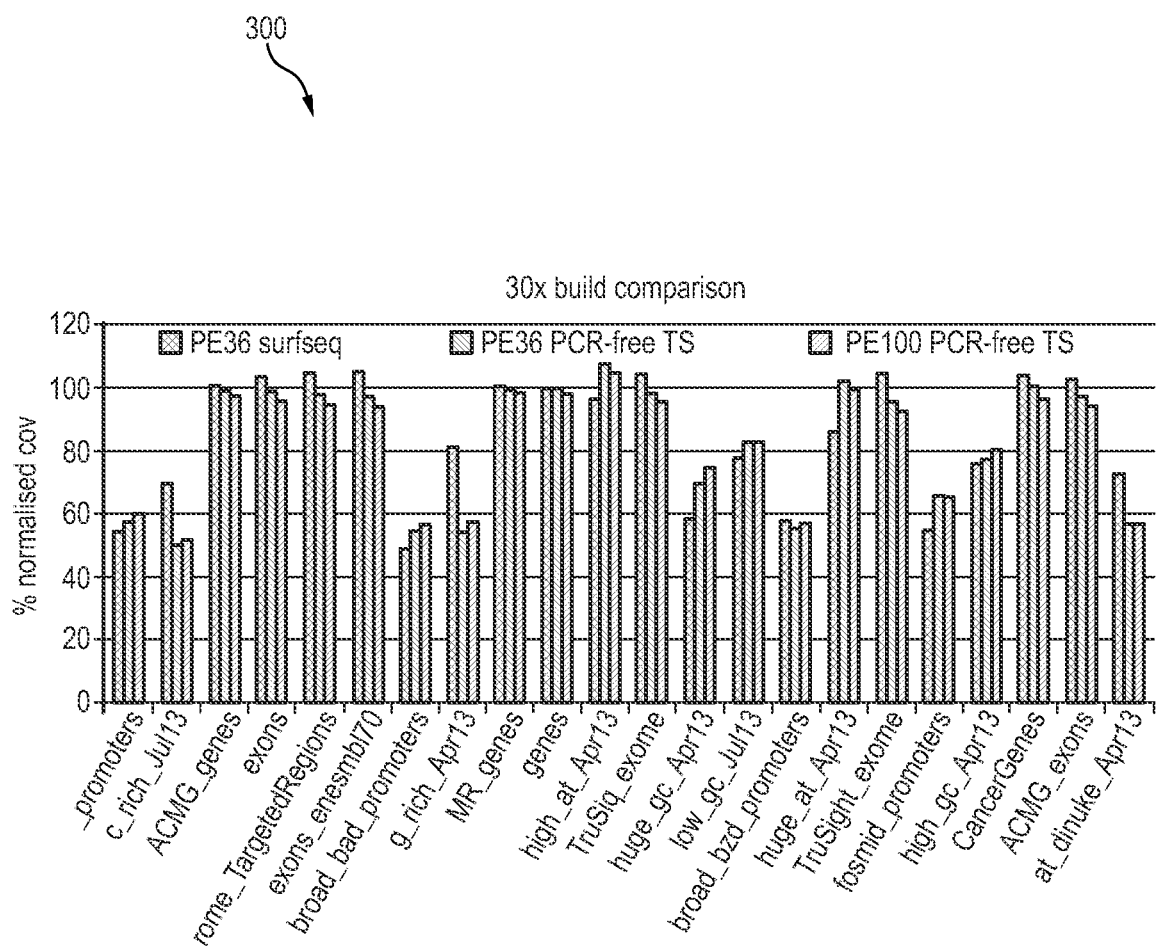
FIG. 13 shows a bar graph of an example of a 30× build comparison used to evaluate the method according to one embodiment.

FIG. 13 shows a bar graph 300 of an example of a 30× build comparison used to evaluate the method according to one embodiment. Bar graph 300 shows the relative coverage (Y axis) of selected features of the human genome (X axis). Each feature was selected because it represents either a sequence of interest (e.g., promoters or exons) or is a challenge for typical next generation sequencing work flows (e.g., GC or AT rich sequences). Each feature may comprise a multitude (i.e., more than one) of locations within the human genome. Bar graph 300 shows three sets of data: a paired 36 base-read from a human library (PE36 surfseq) prepared and sequenced using the method according to one embodiment; a paired 100 base-read from the same human library (PE100 PCR-free TS) prepared by conventional library preparation workflows, but without PCR, and then sequenced conventionally on an Illumina sequencer; and a subsampled data set from the PE100 PCR-free data wherein the reads have been abbreviated from 100 to 36 bases ((PE36 PCR-free TS). In each data set, the coverage of the selected features is normalized against the average coverage depth, which for all libraries in FIG. 13 is 30× coverage depth.

Figure 14:
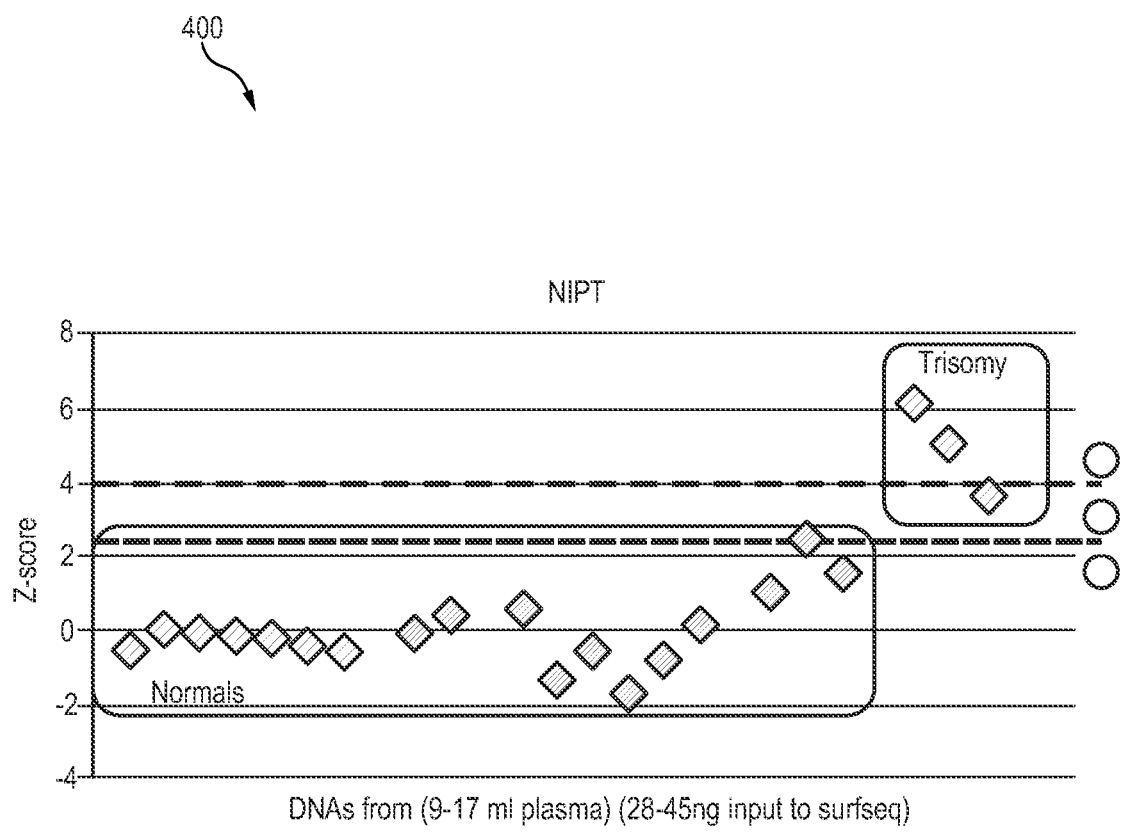
FIG. 14 shows a plot of an example of a non-invasive prenatal test (NIPT) that was performed using the method according to one embodiment.

FIG. 14 shows a plot 400 of an example of a non-invasive prenatal test (NIPT) that was performed using the method according to one embodiment. Plot 400 shows the Z-scores for a panel of samples prepared and sequenced according to the method according to one embodiment. Each point (diamond) on plot 400 represents a sequencing experiment. The seven light gray points represent seven replicate experiments of the same multiplexed pool of NIPT normal control samples. The eleven darker gray points below the Z-score level of 2, represent single NIPT normal control samples. The three dark gray points above the Z-score level of 2 represent individual NIPT samples with verified trisomies. A Z score is a statistical tool that may be used to quantify the probability that a sample has excess chromosomal material (in this instance, Chr 21) relative to the amount of the other chromosomes within the sample. A score of zero indicates that a sample is unlikely to have an imbalance on the number of copies of chromosome 21. A score of 4 or higher indicates a high probability that trisomy 21 is present in the sample, whereas a score between 2 and 4 indicates a suspicion of a chromosomal imbalance but is considered indeterminate.

Bead-Based Tagmentation

The present invention provides methods of tagmenting (fragmenting and tagging) DNA on a bead surface for the construction of a tagmented DNA library.

Figure 15:
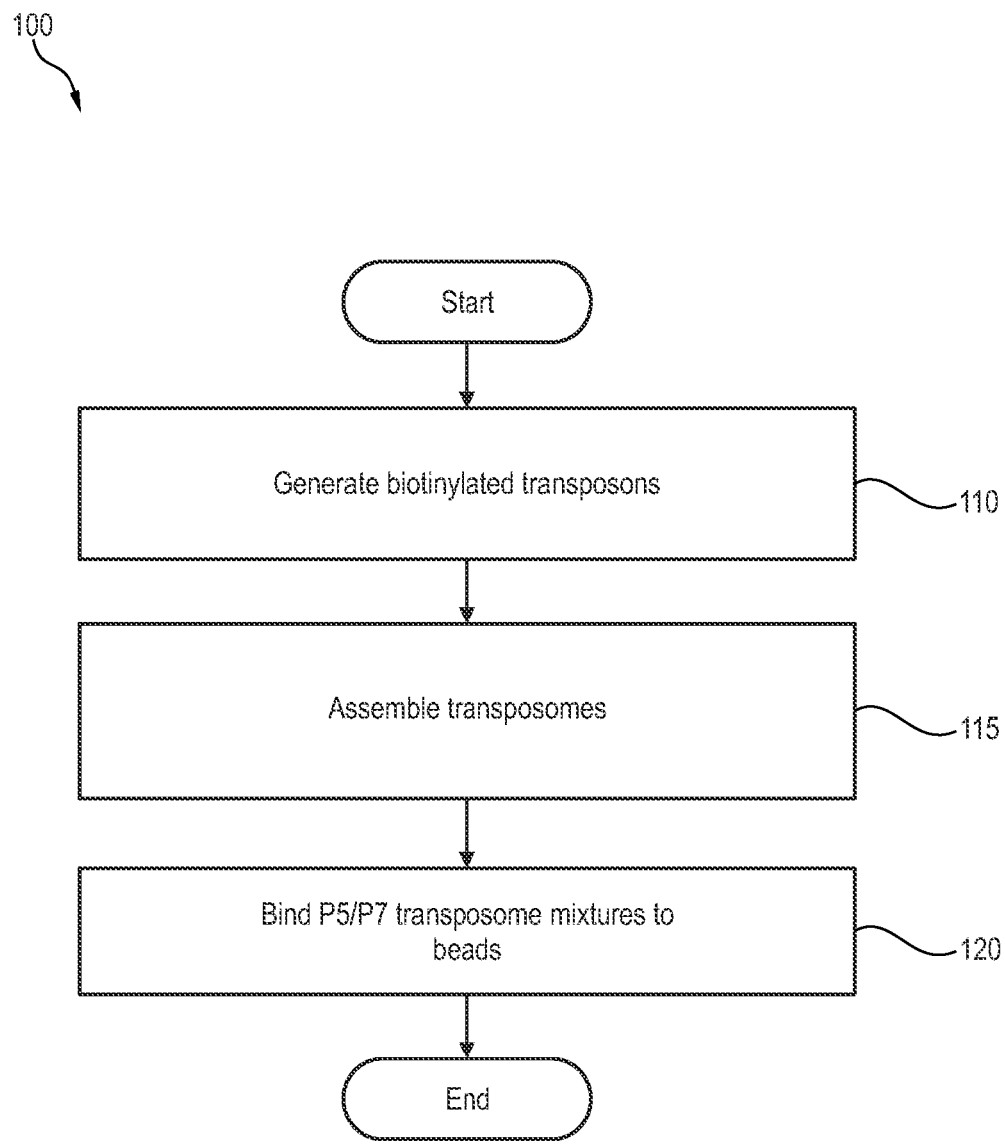
FIG. 15 illustrates a flow diagram of an example of a method of binding transposomes to a bead surface.

FIG. 15 illustrates a flow diagram of an example of a method 100 of binding transposomes to a bead surface. Transposomes may be bound to a bead surface using any DNA chemistry that may be added on the transposon oligonucleotide. In one example, transposomes are bound to a bead surface via a biotin-streptavidin binding complex. Method 100 includes, but is not limited to, the following steps.

At a step 110, P5 and P7 biotinylated transposons are generated. The transposons may also include an index sequence (unique identifier). In another example, only the P5 or only the P7 transposons are biotinylated. In yet another example, the transposons comprise only the ME (mosaic end) sequences or the ME sequences plus additional sequences that are not P5 and P7 sequences. In this example, P5 and P7 sequences are added in a subsequent PCR amplification step.

At a step 115, the transposomes are assembled. The assembled transposomes are a mixture of P5 and P7 transposomes. A mixture of P5 and P7 transposomes are described in more detail with reference to FIGS. 25 and 26.

At a step 120, P5/P7 transposome mixtures are bound to a bead surface. In this example, the beads are streptavidin coated beads and the transposomes are bound to the bead surface via a biotin-streptavidin binding complex. In one example, the beads may be 2.8 μm beads. In another example, the beads may be 1 μm beads. A suspension (e.g., 1 μL) of 1 μm beads provides a greater surface area per volume for transposomes binding. Because of the available surface area for transposomes binding, the number of tagmentation products per reaction is increased.

Figure 16:
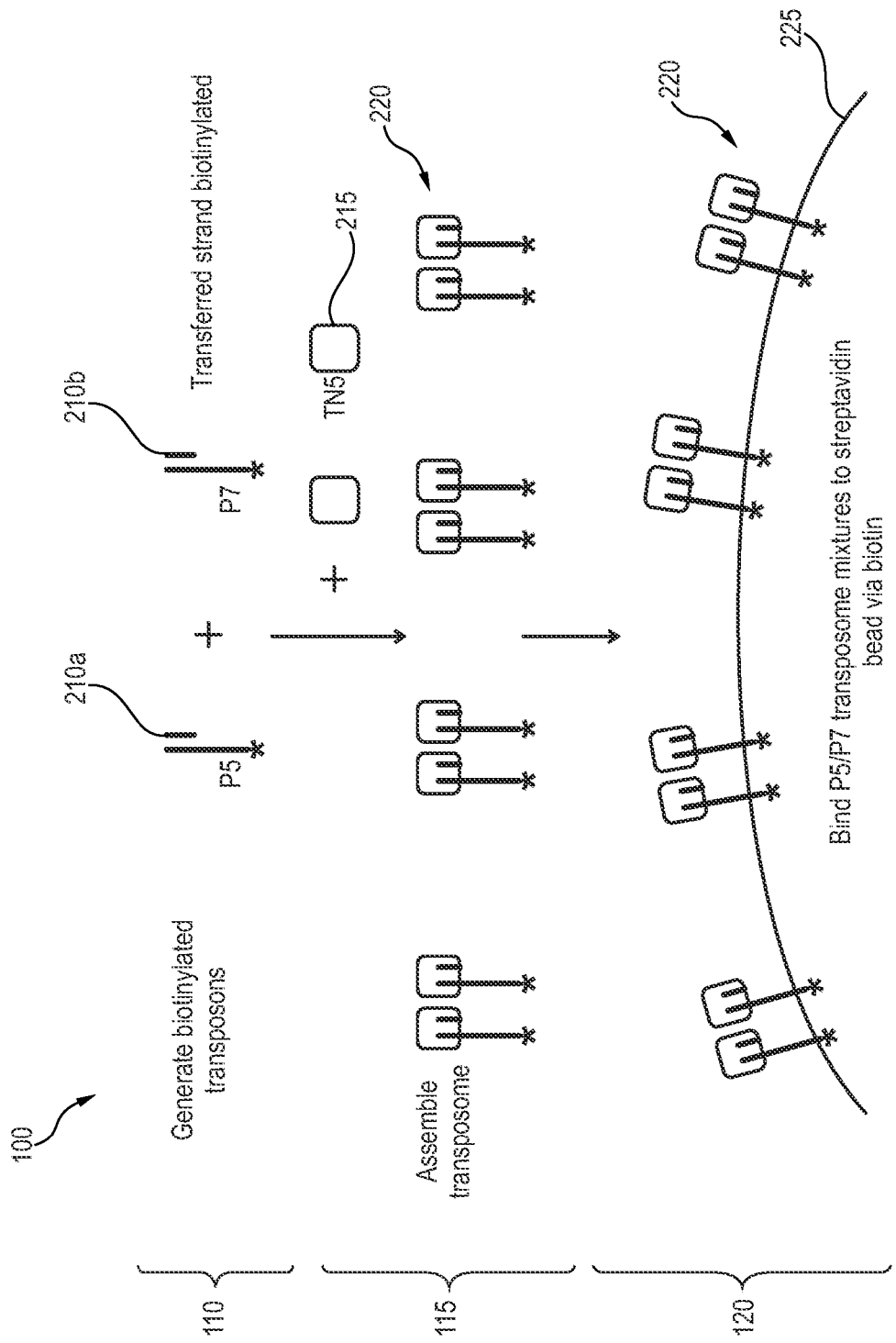
FIG. 16 shows pictorially the steps of the method of FIG. 15.

FIG. 16 shows pictorially the steps 110, 115, and 120 of method 100 of FIG. 15. In this example, the transposons are shown as duplexes. In another example (not shown), another structure such as a hairpin, i.e., a single oligonucleotide with regions of self-complementarity capable of forming a duplex, may be used.

At step 110 of method 100, a plurality of biotinylated P5 transposons 210a and a plurality of P7 transposons 210b are generated. P5 transposons 210a and P7 transposons 210b are biotinylated.

At step 115 of method 100, P5 transposons 210a and P7 transposons 210b are mixed with transposase Tn5 215 to form a plurality of assembled transposomes 220.

At step 120 of method 100, transposomes 220 are bound to a bead 225. Bead 225 is a streptavidin coated bead. Transposomes 220 are bound to bead 225 via a biotin-streptavidin binding complex.

Another example of forming a mixture of transposomes on a bead surface is described with reference to FIGS. 10, 11, 12, and 13. In this example, P5 and P7 oligonucleotides are first bound to a bead surface prior to assembly of transposome complexes.

Figure 17:
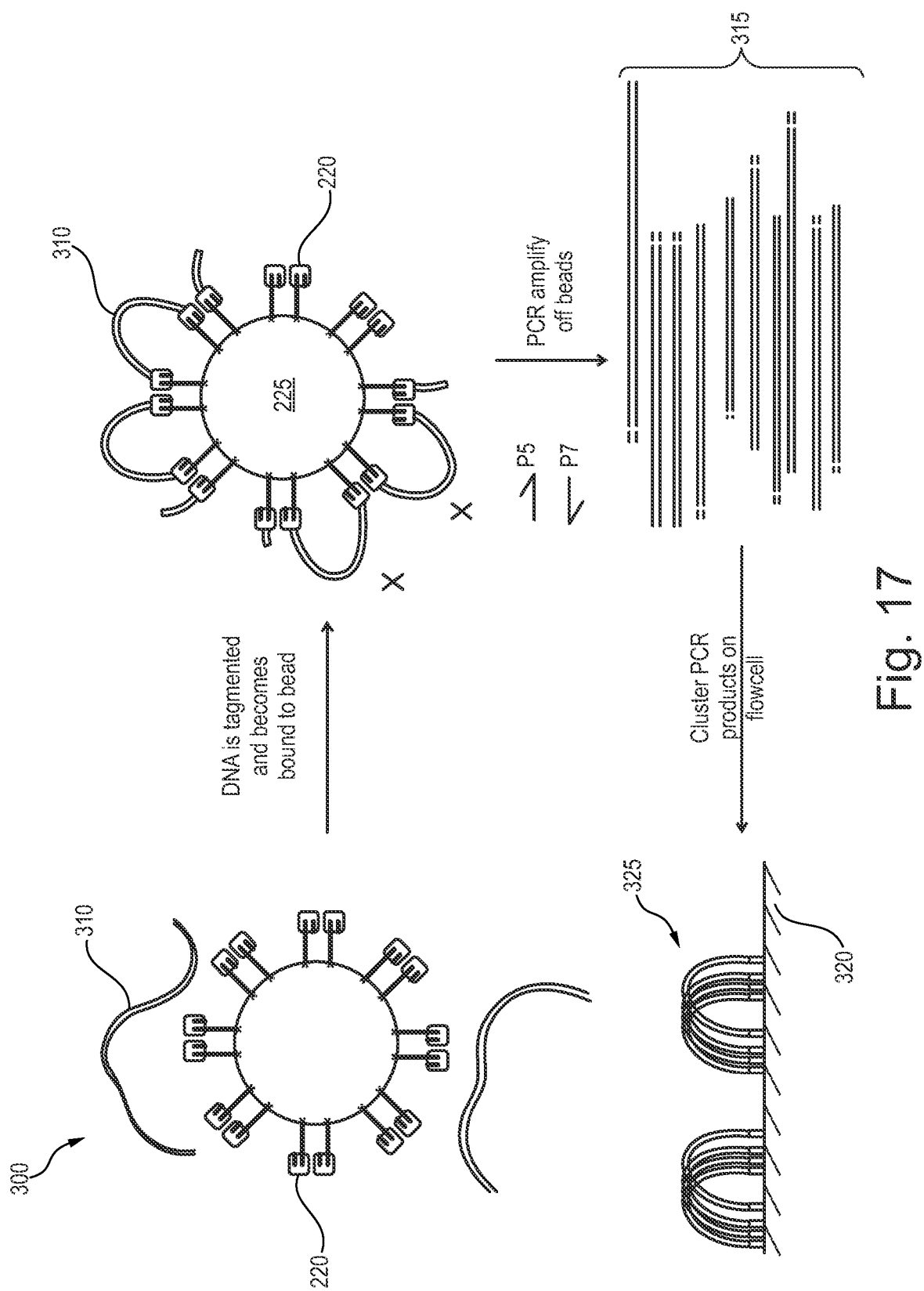
FIG. 17 illustrates a schematic diagram of an example of a tagmentation process on a bead surface.

FIG. 17 illustrates a schematic diagram of an example of a tagmentation process 300 on a bead surface. Shown in process 300 is bead 225 of FIG. 16 with transposomes 220 bound thereon. A solution of DNA 310 is added to a suspension of beads 225. As DNA 310 contacts transposomes 220, the DNA is tagmented (fragmented and tagged) and is bound to beads 225 via transposomes 220. Bound and tagmented DNA 310 may be PCR amplified to generate a pool of bead-free amplicons 315. Amplicons 315 may be transferred to the surface of a flow cell 320. A cluster generation protocol (e.g., a bridge amplification protocol or any other amplification protocol that may be used for cluster generation) may be used to generate a plurality of clusters 325 on the surface of flow cell 320. Clusters 325 are clonal amplification products of tagmented DNA 310. Clusters 325 are now ready for the next step in a sequencing protocol.

FIG. 18 shows a data table 400 of an example of the DNA cluster yield from the bead-based tagmentation process of FIG. 17. In this example, 50, 250, and 1000 ng of human NA12878 DNA were tagmented using the same batch of tagmentation beads (2.8 μm beads). A second 50 ng aliquot of NA12878 DNA was tagmented using a second batch of tagmentation beads (full repeat; 2.8 μm beads). The bead-bound tagmented DNA samples were PCR amplified and purified. An aliquot (5.4 μL) of each purified PCR product (unquantified) was diluted 270 fold to make stock sample solutions of about 50 pM. For each sample, the 50 pM stock solution was diluted to 15, 19, 21, and 24 pM. The diluted samples were loaded onto a flow cell for cluster generation and sequencing. The data show that starting from the same dilution (~50 pM), cluster numbers are between 100-114% for the three different input levels (i.e., 50, 250, and 1000 ng) using the same set of beads. The cluster number for the 50 ng full repeat (with a different batch of beads) was 81%. Different dilutions (15, 19, 21, and 24 pM) yield the same number of clusters within about 10%. The data indicates that the beads are largely controlling the yield and yield is reproducible for different DNA inputs and different repeats.

FIG. 19 shows a data table 500 of another example of the reproducibility of the bead-based tagmentation process of FIG. 17. In this example, six different preparations of indexed beads (indexes 1 through 6; 2.8 μm beads) made at the "same" transposome density were used to prepare tagmented DNA using 50 and 500 ng of input NA12878 DNA. The tagmented DNA was PCR amplified and purified. The 12 purified PCR products were pooled into two mixtures (pool 1 and pool 2) of six for two HiSeq lanes. Each pool includes 3-50 ng and 3-500 ng samples per lane. Data table 500 shows the median insert size and the mean insert size for each indexed sample.

Figure 20A:
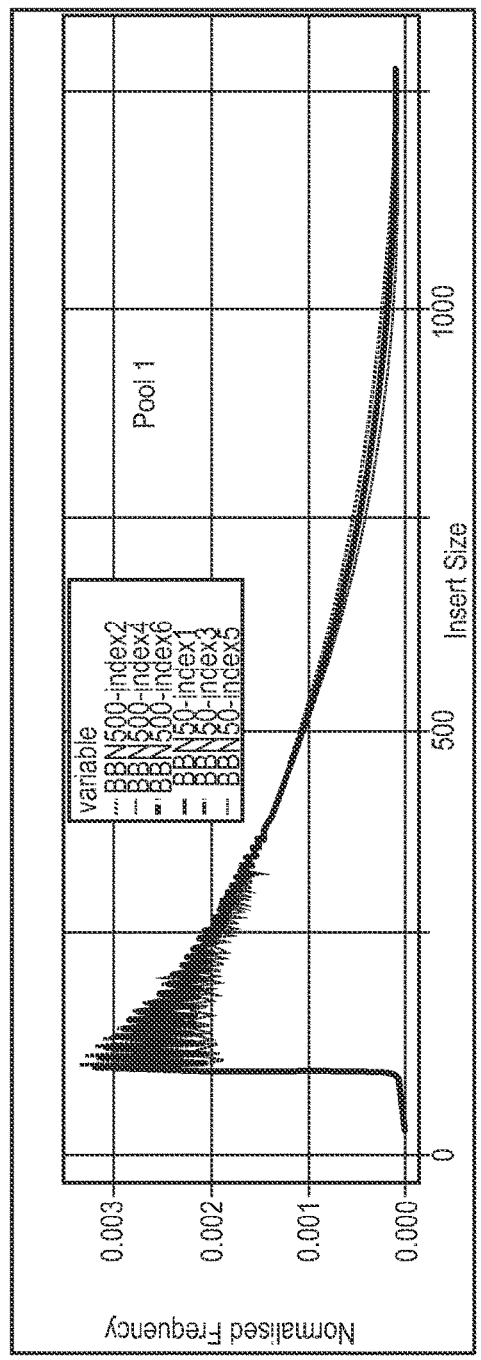
FIGS. 20A and 20B show a plot of the insert size of pool 1 and a plot of the insert size of pool 2, respectively, of the indexed samples of FIG. 19.
Figure 20B:
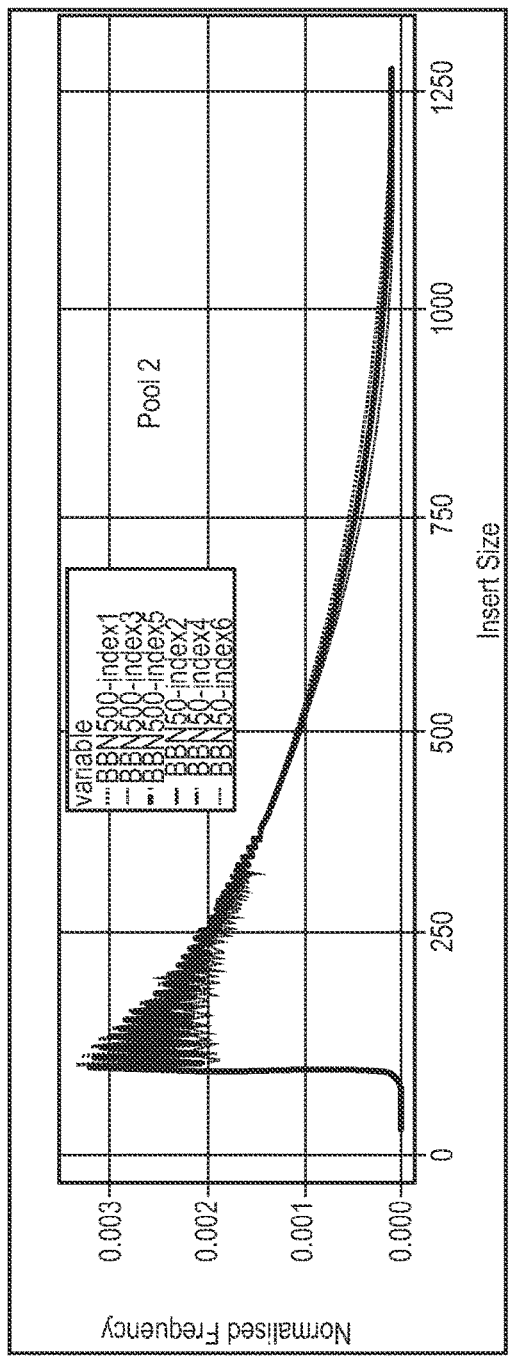

FIGS. 20A and 20B show a plot 600 of the insert size of pool 1 and a plot 650 of the insert size of pool 2, respectively, of the indexed samples of FIG. 19. The data also shows that the insert size is uniform between the six different preparations of indexed beads. Bead-based tagmentation provides a mechanism to control the size of the inserts and DNA yield.

Figure 21:
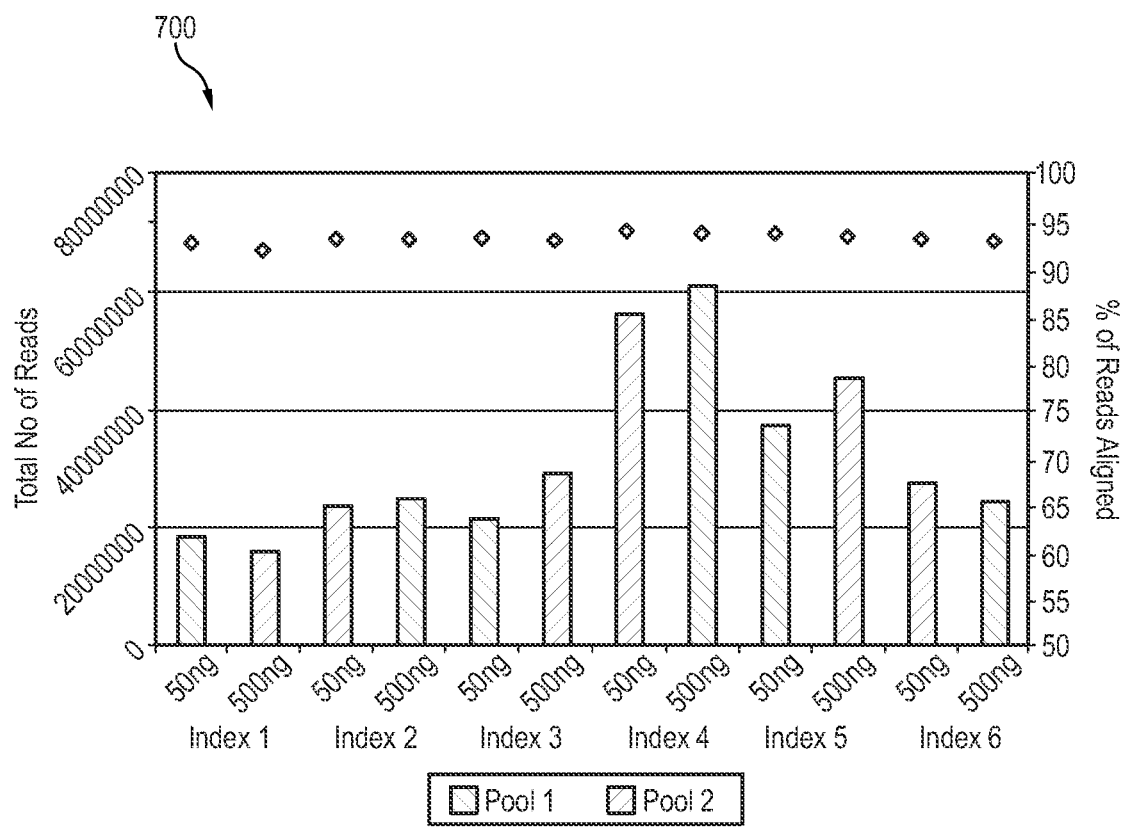
FIG. 21 shows a bar graph of the reproducibility of total number of reads and percent reads aligned for the experiment described in FIG. 19.

FIG. 21 shows a bar graph 700 of the reproducibility of total number of reads and percent reads aligned for the experiment described in FIG. 19. At both inputs (50 ng and 500 ng) the total number of reads is similar for the same indexed bead preparation. Four of the six indexed bead preparations (index 1, 2, 3, and 6) have very similar yields; indexed bead preparations 4 and 5 shown some variability which may be due to the index sequence.

In one application, the bead-based tagmentation process may be used in an exome enrichment assay which includes a tagmentation step, e.g., Illumina's Nextera® Rapid Capture Enrichment protocol. In the current assay, numerous quantification steps are required that slow down the process and are very tedious. In the current exome enrichment assay (i.e., Illumina's Nextera® Rapid Capture Enrichment protocol), solution-based tagmentation (Nextera) is used to fragment the genomic DNA. Gene specific primers are then used to pull down specific gene fragments of interest. Two enrichment cycles are performed and fragments pulled down are then enriched by PCR and sequenced.

To evaluate the use of the bead-based tagmentation process in the exome enrichment assay, human NA12878 DNA was tagmented using 25, 50, 100, 150, 200, and 500 ng of input DNA. A control library (NA00536) was prepared from 50 ng input DNA according to the standard protocol. Each DNA input had a different index (unique identifier). Ten cycles of PCR using enhanced polymerase mastermix (EPM) were used to match standard methods and to ensure a sufficient amount of fragments were present for pulldown. The amplification protocol was 3 minutes at 72° C., 30 seconds at 98° C., followed by 10 cycles of 10 seconds at 98° C., 30 seconds at 65° C., and 1 minute at 72° C. The samples were then held at 10° C. The samples were then processed through the exome enrichment pulldown process and sequenced.

FIGS. 22A, 22B, and 22C show a plot 800 of insert size in a control library, a plot 820 of insert size in a bead-based tagmented library, and a summary data table 840, respectively, in the exome enrichment assay. The data show that the bead-based tagmentation libraries have a wider insert size spread compared to the control library, but the insert size is very similar irrespective of the DNA input for the Nagini samples (as seen previously).

Figure 23A:
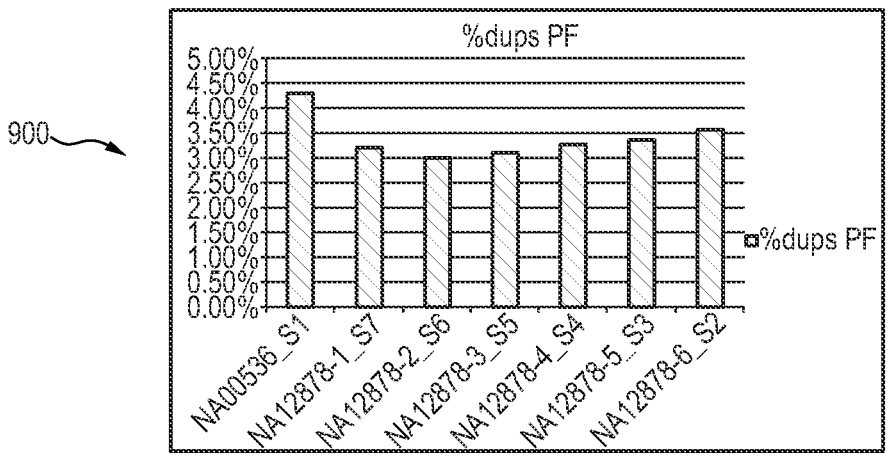
FIGS. 23A, 23B, and 23C show a bar graph of the fraction of dups PF, a bar graph of the fraction of selected bases, and bar graph of PCT usable bases on target, respectively, in the exome enrichment assay.
Figure 23B:
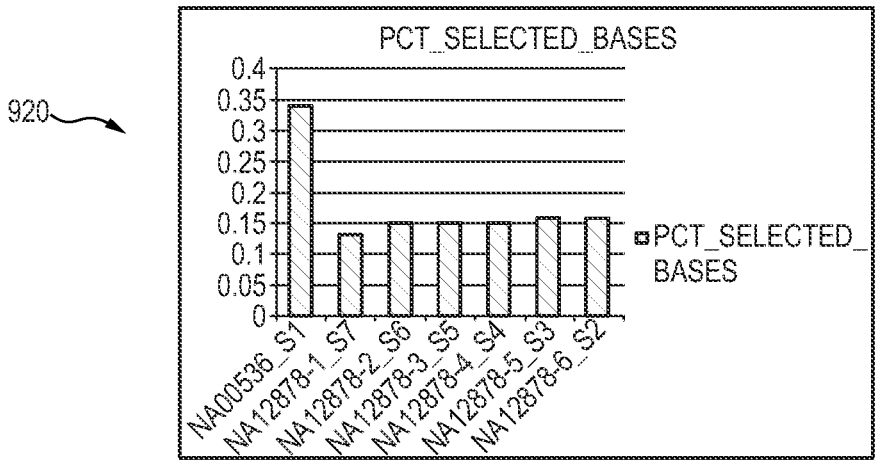
Figure 23C:
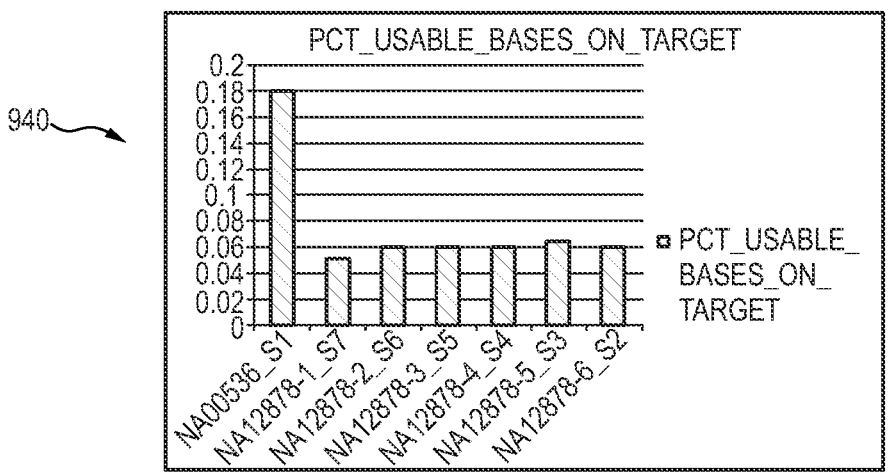

FIGS. 23A, 23B, and 23C show a bar graph 900 of percent dups PF, a bar graph 920 of PCT selected bases, and bar graph 940 of PCT usable bases on target, respectively, in the exome enrichment assay of FIGS. 22A, 22B, and 22C. Referring to FIG. 23A, the percent duplicates (dups) PF (passing filters) is a measure of how many reads are duplicated elsewhere on the flow cell. This number will ideally be low (as here) to ensure that all clusters are bringing useful data to the results.

Referring to FIG. 23B, PCT selected bases is a measure of the ratio of reads that sequence at or near the site of interest which should have been enriched during the enrichment process. Ideally this number will be close to 1 to reflect the success of the enrichment process and show that reads that should not be enriched do not get through the process.

Referring to FIG. 23C, the PCT usable bases on target is a measure of the ratio of reads that actually sequence over the particular base of interest within the enriched region. Ideally all enriched reads would sequence over the base of interest within the enriched read, but due to the random nature of the tagmentation and the variable length of the inserts, reads may be enriched that do not end up being sequenced over the area of interest.

Two techniques may be used to optimize the insert size distribution. In one example, an SPRI clean-up may be used to remove fragments that are too small or too large. SPRI clean-up is a process of removing fragments that are larger or smaller than the desired size, by selective DNA precipitation based on size and either retention of the precipitated or non-precipitated DNA as desired (i.e., a first step is to precipitate only DNA that is larger than the desired size and retain the soluble smaller fragments). The smaller fragments are then further precipitated and this time the very small fragments that are not wanted (still in solution) are removed and the precipitated DNA is retained, washed and then resolubilised to give a desired size range of DNA. In another example, the spacing of active transposomes on the bead surface may be used to control the insert size distribution. For example, gaps on the bead surface may be filled with inactive transposomes (e.g., transposomes with inactive transposons).

Contiguity of the bead-based tagmentation process was assessed. Table 3 shows the number of times 0, 1, 2, or 3 reads occur within a 1000 bp windows sharing an index. Beads were generated with 9 different indexed transposomes and used to tagment a small amount of human DNA. Reads were generated, aligned, and analyzed for the number of reads within a 1000 bp or 10 Kb window that shared the same index. Some reads within a small window sharing an index may be generated by chance and a prediction of how many times this is likely to occur is given in the "Random" row of Table 3 and Table 4. The numbers in the "Bead" row show the actual number of 1000 bp (Table 3) or 10 Kb (Table 2) windows that share an index. As shown in Table 3 and Table 4, the actual number of times the same index was found within 1000 bp or 10 Kb window is significantly greater than expected in the random case. "0" windows show all the times a particular 1000 bp window had no indexed reads mapping to it. The number is largest here because only a very small amount of the human genome was sequence and most windows have no reads aligning to them. "1" is the number of times just one read maps to a 1000 bp (or 10 Kb) window; "2" the number of times 2 reads share an index within a 1000 bp (or 10 KB) window, etc. This data suggests that in over 1400 cases the same piece of DNA (over 10 Kb) is being tagmented by the same bead at least twice and up to 5 times, out of about 15000 tagmentation events. Since the fragments share an index, they are unlikely to be there by chance, but are coming from the same bead.

TABLE 3

Number of reads in a 1000 bp windows sharing an index

|  | 0 | 1 | 2 | 3 |
| --- | --- | --- | --- | --- |
| Bead | 25913666 | 15220 | 305 | 7 |
| Random | 25913334 | 15855 | 9 | 0 |

Table 4 shows the number of reads (up to 5) within a 10 kb windows sharing an index.

TABLE 4

Number of reads in a 10 kb windows sharing an index

|  | 0 | 1 | 2 | 3 | 4 | 5 |
| --- | --- | --- | --- | --- | --- | --- |
| Bead | 2578669 | 12683 | 1267 | 169 | 28 | 3 |
| Random | 2577012 | 15742 | 64 | 1 | 0 | 0 |

In another application, the bead-based tagmentation process may be used for tagmentation of cell free DNA (cfDNA) in cfDNA assays.

In another embodiment, the transposomes may be bound to any solid surface, such as the walls of a microfuge tube.

Figure 24:
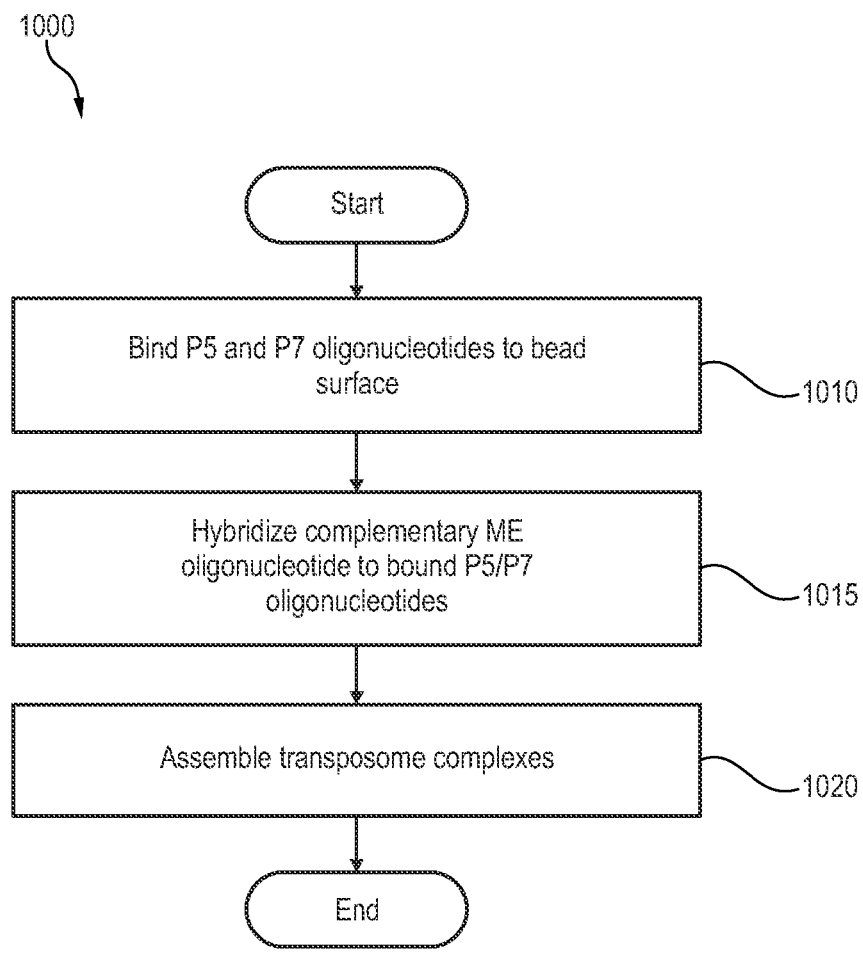
FIG. 24 illustrates a flow diagram of an example of a method of forming transposome complexes on a bead surface.

In another example of forming a mixture of transposome complexes on a bead surface, oligonucleotides are first bound to a bead surface prior to transposome assembly. FIG. 24 illustrates a flow diagram of an example of a method 1000 of forming transposome complexes on a bead surface. Method 1000 includes, but is not limited to, the following steps.

Figure 25:
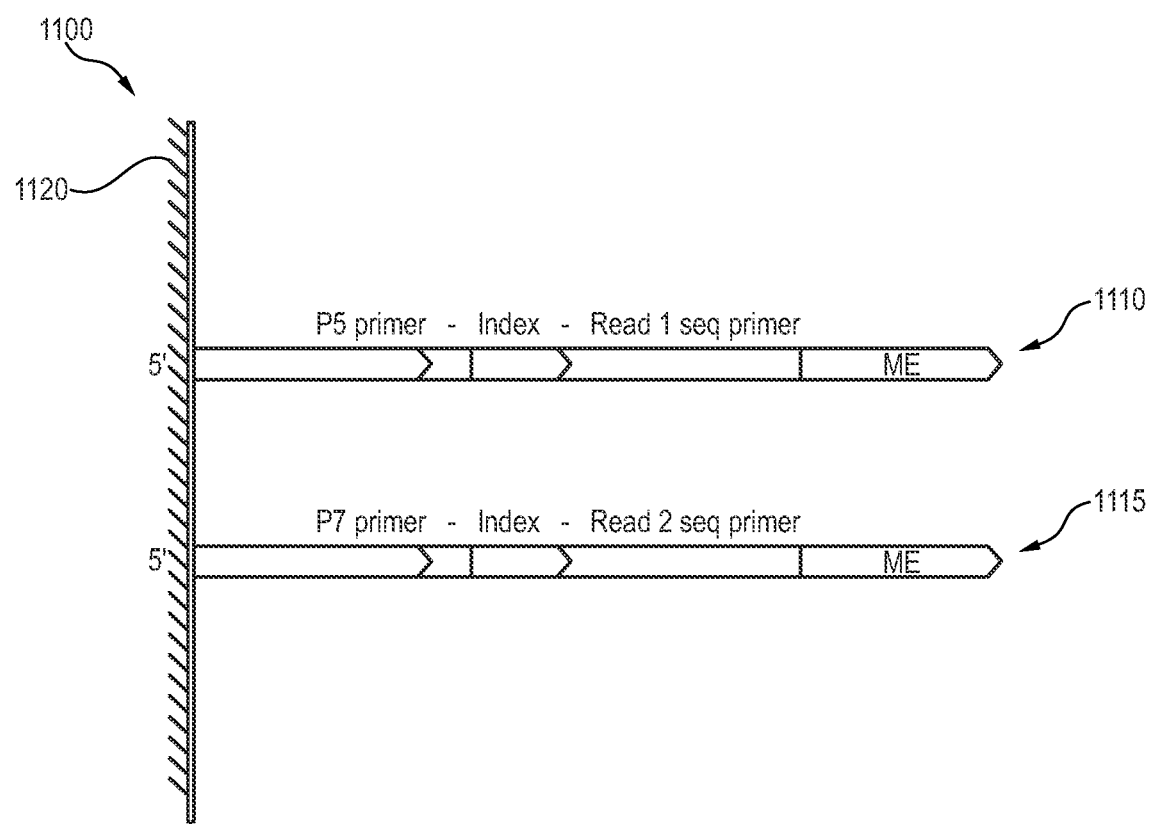
FIGS. 25, 26, and 27 show pictorially the steps of the method of FIG. 24.

At a step 1010, P5 and P7 oligonucleotides are bound to a bead surface. In one example, the P5 and P7 oligonucleotides are biotinylated and the bead is a streptavidin coated bead. This step is also shown pictorially in schematic diagram 1100 of FIG. 25. Referring now to FIG. 25, a P5 oligonucleotide 1110 and a P7 oligonucleotide 1115 are bound to the surface of a bead 1120. In this example, a single P5 oligonucleotide 1110 and a single P7 oligonucleotide 1115 are bound to the surface of bead 1120, but any number of P5 oligonucleotides 1110 and/or P7 oligonucleotides 1115 may be bound to the surface of a plurality of beads 1120. In one example, P5 oligonucleotide 1110 comprises a P5 primer sequence, an index sequence (unique identifier), a read 1 sequencing primer sequence and a mosaic end (ME) sequence. In this example, P7 oligonucleotide 1115 comprises a P7 primer sequence, an index sequence (unique identifier), a read 2 sequencing primer sequence and an ME sequence. In another example (not shown), an index sequence is present in only P5 oligonucleotide 1110. In yet another example (not shown), an index sequence is present in only the P7 oligonucleotide 1115. In yet another example (not shown), an index sequence is absent in both P5 oligonucleotide 1110 and P7 oligonucleotide 1115.

Figure 26:
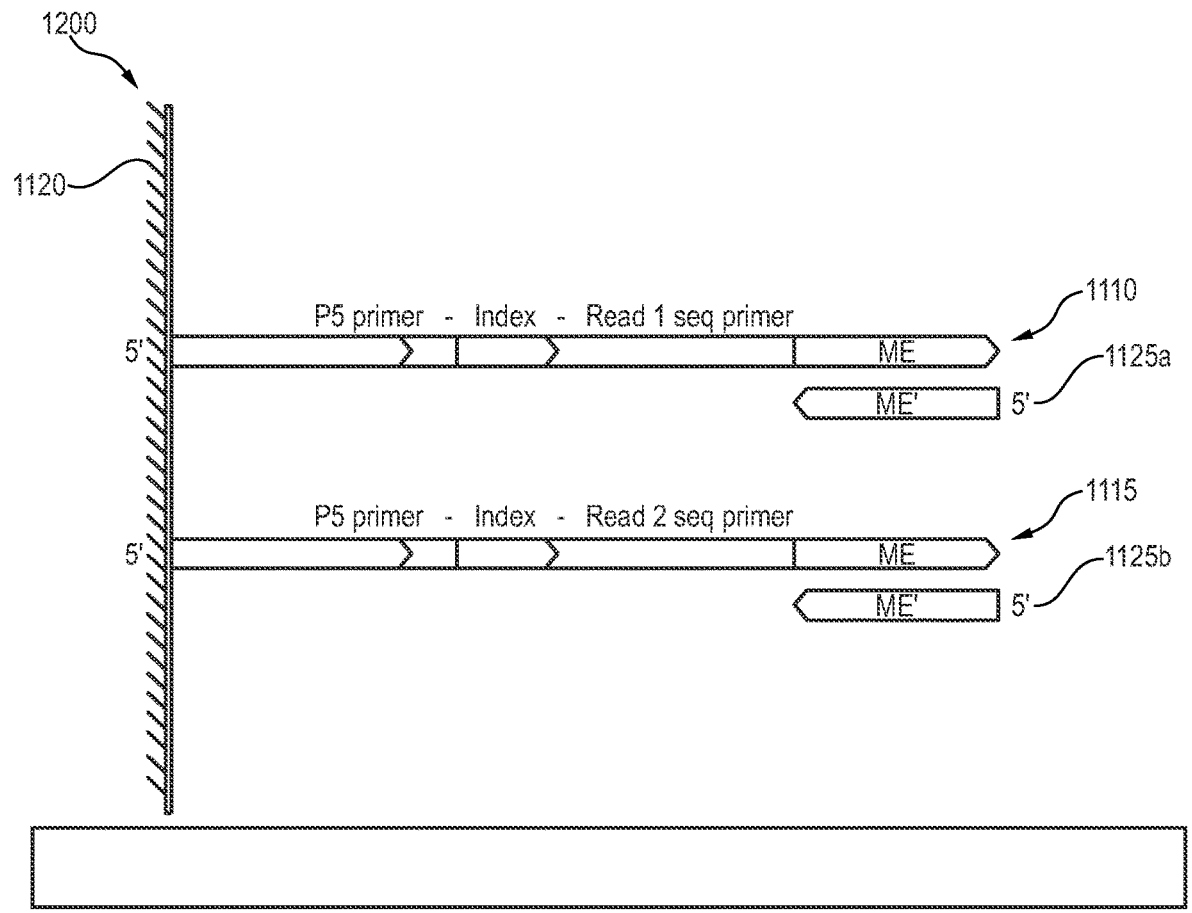

At a step 1015, complementary mosaic end (ME') oligonucleotides are hybridized to the bead-bound P5 and P7 oligonucleotides. This step is also shown pictorially in schematic diagram 1200 of FIG. 26. Referring now to FIG. 26, complementary ME sequences (ME') 1125 are hybrid to P5 oligonucleotide 1110 and P7 oligonucleotide 1115. Complementary ME sequences (ME') 1125 (e.g., complementary ME sequences (ME') 1125a and complementary ME sequences (ME') 1125b) hybridize to the ME sequences in P5 oligonucleotide 1110 and P7 oligonucleotide 1115, respectively. Complementary ME sequence (ME') 1125 is typically about 15 bases in length and phosphorylated at its 5' end.

Figure 27:
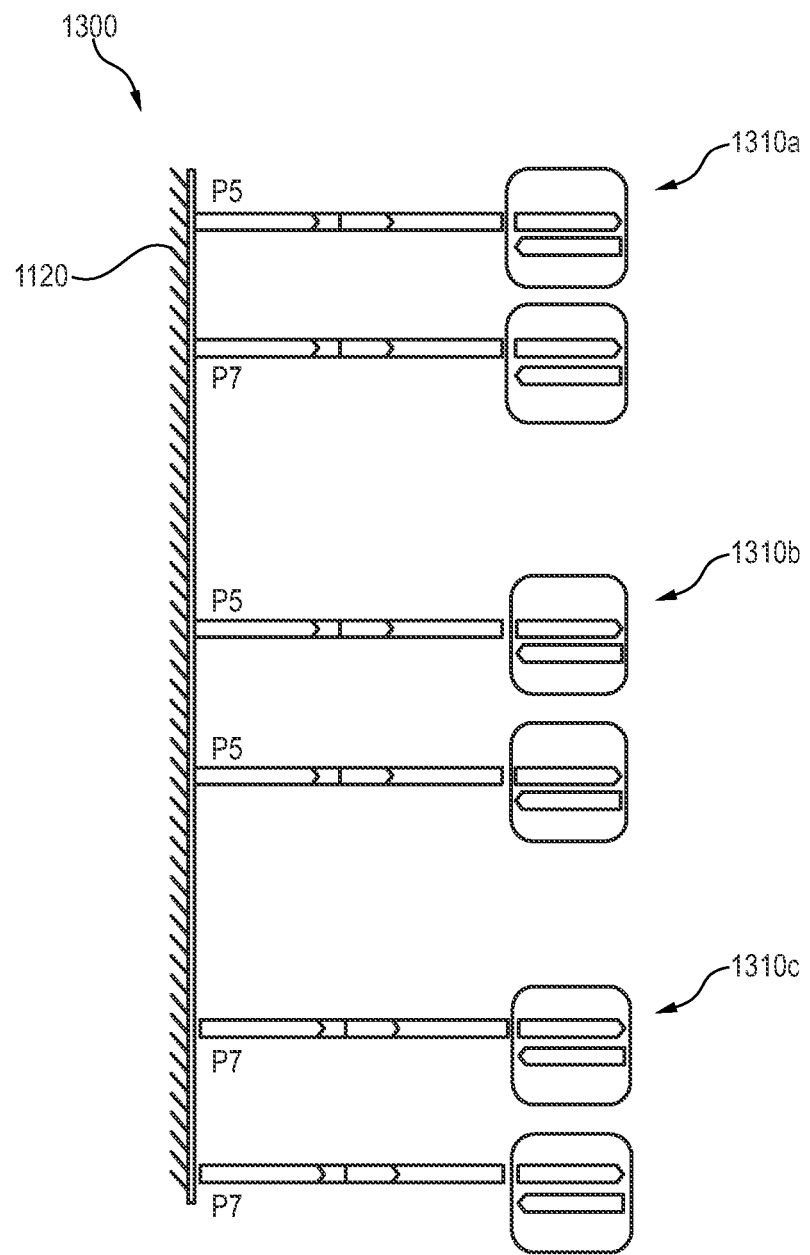

At a step 1020, transposase enzyme is added to the bead-bound oligonucleotides to form a mixture of bead-bound transposome complexes. This step is also shown pictorially in schematic diagram 1300 of FIG. 27. Referring now to FIG. 27, transposase enzyme is added to form a plurality of transposome complexes 1310. In this example, transposome complex 1310 is a duplex structure that comprises transposase enzyme, two surface-bound oligonucleotide sequences, and their hybridized complementary ME sequences (ME') 1125. For example, transposome complex 1310a comprises P5 oligonucleotide 1110 hybridized to complementary ME sequence (ME') 1125 and P7 oligonucleotide 1115 hybridized to complementary ME sequence (ME') 1125 (i.e., P5:P7); transposome complex 1310b comprises two P5 oligonucleotides 1110 hybridized to complementary ME sequences (ME') 1125 (i.e., P5:P5); and transposome complex 1310c comprises two P7 oligonucleotides 1115 hybridized to complementary ME sequences (ME') 1125 (i.e., P7:P7). The ratio of P5:P5, P7:P7, and P5:P7 transposome complexes may be, for example, 25:25:50, respectively.

Figure 28:
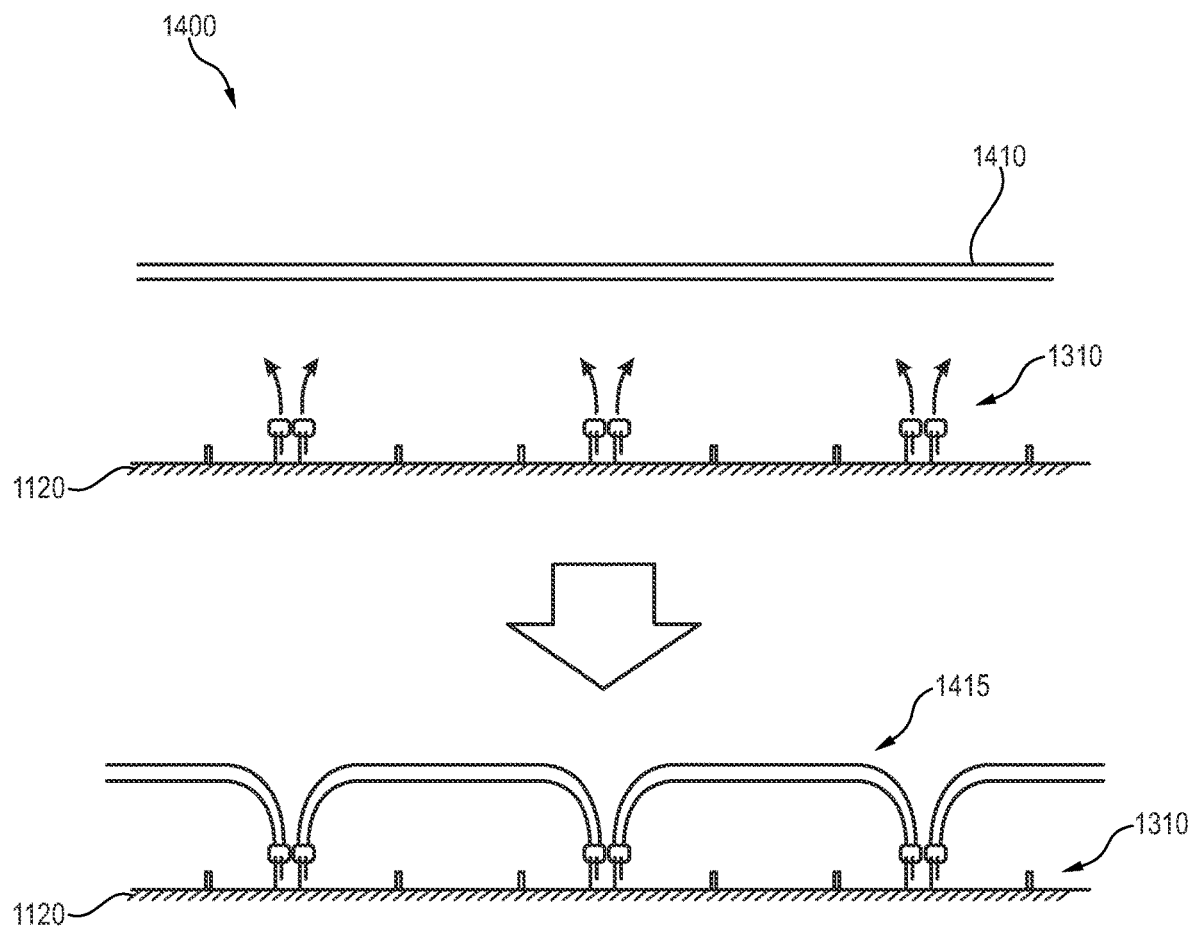
FIG. 28 shows a schematic diagram of a tagmentation process using the transposome coated bead shown in FIG. 27.

FIG. 28 shows a schematic diagram 1400 of a tagmentation process using the transposome coated bead 1120 of FIG. 27. In this example, when bead 1120 with transposome complexes 1310 thereon is added to a solution of DNA 1410 in a tagmentation buffer, tagmentation occurs and the DNA is linked to the surface of bead 1120 via transposomes 1310. Successive tagmentation of DNA 1410 results in a plurality of bridged molecules 1415 between transposomes 1310. The length of bridged molecules 1415 may be dependent on the density of transposome complexes 1310 on the surface of bead 1120. In one example, the density of transposome complexes 1310 on the surface of bead 1120 may be tuned by varying the amount of P5 and P7 oligonucleotides bound to the surface of bead 1120 in step 1010 of method 100 of FIG. 24. In another example, the density of transposome complexes 1310 on the surface of bead 1120 may be tuned by varying the amount of complementary ME sequence (ME') hybridized to P5 and P7 oligonucleotides in step 1015 of method 1000 of FIG. 24. In yet another example, the density of transposome complexes 1310 on the surface of bead 1120 may be tuned by varying the amount of transposase enzyme added in step 1020 of method 1000 of FIG. 15. The length of bridged molecules 1415 is independent of the quantity of beads 1120 with transposome complexes 1310 bound thereon used in a tagmentation reaction. Similarly, adding more or less DNA 1410 in a tagmentation reaction does not alter the size of the final tagmented product, but may affect the yield of the reaction.

In one example, bead 1120 is a paramagnetic bead. In this example, purification of the tagmentation reaction is readily achieved by immobilizing beads 1120 with a magnet and washing. Therefore, tagmentation and subsequent PCR amplification may be performed in a single tube ("one-pot") reaction.

Throughout this application various publications, patents and/or patent applications have been referenced. The disclosure of these publications in their entireties is hereby incorporated by reference in this application.

The term comprising is intended herein to be open-ended, including not only the recited elements, but further encompassing any additional elements.

A number of embodiments have been described. Nevertheless, it will be understood that various modifications may be made. Accordingly, other embodiments are within the scope of the following claims.

What is claimed is:

1. A method of preparing amplified DNA fragments immobilized on a solid support comprising:
   (a) providing a solid support coated with immobilized transposome complexes, wherein the solid support comprises dried tagmentation reagents configured to be reconstituted to form a tagmentation reaction mixture upon contact with a liquid sample, wherein the tagmentation reagents comprise transposome complexes and a tagmentation buffer, wherein the immobilized transposome complexes are prepared by:
      (i) combining purified transposases with transposons to prepare transposome complexes and then immobilizing the transposome complexes to the solid support, or
      (ii) immobilizing transposons to the solid support and then adding purified transposases to prepare immobilized transposome complexes;
   (b) applying a liquid sample comprising target nucleic acid to the solid support under conditions suitable for tagmentation, thereby forming a tagmentation reaction mixture and immobilizing fragments of the target nucleic acid to the solid support;
   (c) washing the solid support to remove any unbound nucleic acids; and
   (d) amplifying the immobilized fragments.

2. The method of claim 1, wherein the solid support comprises a sample tube.

3. The method of claim 1, wherein the solid support is coated with streptavidin and the transposome complexes comprise biotin.

4. The method of claim 1, wherein the liquid sample comprises a crude cell lysate or purified genomic DNA.

5. The method of claim 1, wherein the transposome complexes are duplexes, wherein each duplex comprises a transposase enzyme and two surface-bound oligonucleotide sequences.

6. The method of claim 1, wherein the method provides for uniform fragment size and library yield of the immobilized fragments.

7. The method of claim 6, wherein the density of transposomes immobilized on the solid surface is selected to modulate fragment size and library yield of the immobilized fragments.

8. The method of claim 1, further comprising sequencing the amplified fragments after the amplifying.

9. The method of claim 8, wherein the amplified fragments are purified before the sequencing.

10. The method of claim 1, wherein the solid support comprises a membrane.

11. The method of claim 10, wherein the membrane comprises filter paper.

12. The method of claim 10, wherein the membrane is part of a lateral flow device for tagmentation that includes different zones with immobilized reagents for tagmentation, wherein the lateral flow device comprises:
   a sample deposition region;
   a buffer region; and
   a tagmentation region comprising the solid support comprising the immobilized transposome complexes; wherein the solid support is configured for sample migration via capillary action from the sample deposition region to the tagmentation region.

13. The method of claim 12, wherein the buffer region comprises lysis reagents for lysing sample cells and releasing nucleic acid into solution.

14. The method of claim 12, wherein the buffer region comprises dried sample reagents configured to be reconstituted to form a lysis buffer upon contact with a liquid sample.

15. The method of claim 12, wherein step (b) comprises applying a liquid sample to the sample deposition region; wherein the liquid sample migrates via capillary action from the sample deposition region to the tagmentation region and nucleic acid in the liquid sample is tagmented and immobilized by the immobilized transposomes.

16. The method of claim 15, wherein the liquid sample migrates via capillary action from the sample deposition region to the buffer region and cells in the liquid sample are lysed by reconstituted lysis buffer, thereby releasing nucleic acid into solution.

* * * * *